United States Patent [19]
Lobl et al.

[11] Patent Number: 5,821,329
[45] Date of Patent: Oct. 13, 1998

[54] CYCLIC PEPTIDE INHIBITORS OF $\beta_1$ AND $\beta_2$ INTEGRIN-MEDIATED ADHESION

[75] Inventors: Thomas J. Lobl, Encinitas; Shiu-Lan Chiang; Wolfgang Scholz, both of San Diego; Nancy Delaet, San Diego; Pina Cardarelli, Solana Beach, all of Calif.

[73] Assignee: Tanabe Seiyaku Co., Ltd., Osaka, Japan

[21] Appl. No.: 738,838

[22] Filed: Oct. 28, 1996

Related U.S. Application Data

[63] Continuation-in-part of PCT/US96/10186 Jun. 6, 1996.
[51] Int. Cl.[6] .............................. A61K 38/12; C07K 5/00; C07K 7/00
[52] U.S. Cl. .......................... 530/317; 530/318; 530/328; 530/329; 530/330; 514/11; 514/16; 514/17; 514/18
[58] Field of Search ...................... 530/317, 318, 530/328, 329, 330; 514/11, 16, 17, 18

[56] References Cited

FOREIGN PATENT DOCUMENTS 9200995   1/1992   WIPO .
9415958   7/1994   WIPO .

*Primary Examiner*—Ponnathapura Achutamurthy
*Assistant Examiner*—Padmashri Ponnalori
*Attorney, Agent, or Firm*—Birch, Stewart, Kolasch & Birch, LLP

[57] ABSTRACT

The present invention describes cyclic peptide compounds which modulate integrin mediated adhesion. These compounds can inhibit both $\beta_1$ and $\beta_2$ mediated adhesion. The invention further relates to therapeutic uses for these compounds in the treatment of adhesion related pathologies.

45 Claims, No Drawings

CYCLIC PEPTIDE INHIBITORS OF $\beta_1$ AND $\beta_2$ INTEGRIN-MEDIATED ADHESION

RELATED APPLICATIONS

The present application is a Continuation-In-Part of International application Ser. No. PCT/US96/10186, filed Jun. 6, 1996 and designating the United States, which in turn claims priority of U.S. application Ser. No. 08/479,411, filed Jun. 7, 1995, now abandoned. The entire contents of each of these applications is hereby incorporated by reference.

BACKGROUND OF THE INVENTION

1. Field of Invention

The present invention relates to novel cyclic peptides and peptidomimetic compounds which are characterized by cell adhesion modulation activity.

2. Description of Related Art

Vascular endothelial cells form the interface between blood and tissues and control the passage of leukocytes as well as plasma fluid into tissues. A variety of signals generated at the site of inflammation can activate both endothelial cells as well as circulating leukocytes so that they become more adhesive to one another. Activation of endothelium and leukocytes initiates a complex adhesion cascade. This adhesion cascade involves the "tethering" of the leukocytes to the endothelium, after which they "roll" along the endothelial surface and finally strongly adhere and migrate into tissue to perform host defense functions. Several adhesion molecules, belonging to a super gene family consisting of non-covalently associated heterodimeric proteins called integrins, have been identified as being involved in leukocyte-endothelial cell interactions.

The $\beta_2$ integrin subfamily includes LFA-1 (CD11a/CD18), Mac-1 (CD11b/CD18, CR3) and p150/95 (CD11c/CD18, CR4). The known ligands for LFA-1 are ICAM-1, ICAM-2 and ICAM-3. The Intracellular Adhesion Molecules (ICAM) are members of the Ig gene superfamily. ICAM-1 is the most ubiquitous of the ICAMs, being expressed in low levels on most peripheral blood leukocytes as well as endothelial cells, fibroblasts and dendritic cells. Cytokine activation of endothelial cells induces a dramatic increase in the expression of ICAM-1 and LFA-1/ICAM-1 interactions which are integral to both lymphocyte adhesion and transmigration through the endothelial barrier; Dustin, M. L. et al, *J. Immunol.*, 137, 245–254 (1986). ICAM-2 is primarily constitutively expressed on endothelial cells; de Fougerolles, A. R. et al, *J. Exp. Med.*, 174, 253–267 (1991), and ICAM-3 is largely found on resting lymphocytes, monocytes and neutrophils; and shows increased expression upon T cell activation; de Fougerolles, A. R. and Springer, T. A., *J. Exp. Med.*, 175, 185–190 (1992).

In addition to its critical role in mediating cellular adhesion, ICAM-1 has also been shown to act as a receptor for a subgroup of rhinoviruses known as the major groups, and soluble ICAM-1 has been shown to act as specific inhibitor of rhinovirus infection; Martin, S. D. et al, *Nature*, 344, 70–72 (1990). A compound which blocks the interaction of rhinovirus with ICAM-1 may be a powerful pharmacological agent for the prevention and treatment of colds and secondary complications arising from rhinovirus infection.

Members of the $\beta_1$ integrin subfamily include $\alpha_1\beta_1$, $\alpha_2\beta_1$, $\alpha_3\beta_1$, $\alpha_4\beta_1$ (VLA-4, CD49d/CD29), $\alpha_7\beta_1$, $\alpha_5\beta_1$ (VLA-5, CD49e/CD29), $\alpha_6\beta_1$, $\alpha_8\beta_1$ and $\alpha_v\beta_1$ (CD51/CD29). $\alpha_4\beta_1$ binds to both fibronectin and the cytokine inducible molecule on endothelial cells termed vascular cell adhesion molecule (VCAM). $\alpha_4\beta_1$/VCAM-1 interaction has been shown to be involved with lymphocyte extravasation at sites of chronic inflammation; Elices, M. J. et al, *Cell*, 60, 577–584 (1990).

An additional member of the "CAM" family of integrin ligands which plays an important role in adhesion is Mad-CAM (mucosal addressin cell adhesion molecule). This molecule which is primarily expressed on Peyer's Patch HEV and lamina propia vessels, is involved with the homing of lymphoid subsets through interactions with the integrin $\alpha_4\beta_7$; Streeter, P. R. et al, *Nature*, 331, 41 (1988).

Data support important roles for both $\alpha_4\beta_1$/VCAM and LFA-1/ICAM in inflammation. In vitro data show that antibodies to $\alpha_4$ block adhesion of lymphocytes to synovial endothelial cells; this adhesion plays a potential role in rheumatoid arthritis (van Dinther-Janssen et al, *J. Immunol.*, 147, 4207 (1991)). Studies in which monoclonal antibodies to $\alpha_4$ block adhesion of basophils and eosinophils to cytokine activated endothelial cells (Walsh et al, *J. Immunol.*, 146, 3419 (1991); Bochner et al, *J. Exp. Med.*, 173, 1553 (1991)) imply a potential role of $\alpha_4$ in allergy and asthma. Additionally, in vivo studies have shown that experimental autoimmune encephalomyelitis can be blocked by anti-$\alpha_4$ monoclonal antibodies (Yednock et al., *Nature*, 356, 63 (1992)). Migration of leukocytes to an inflammatory site can also be blocked by anti-$\alpha_4$ monoclonal antibodies (Issekutz et al., *J. Immunol.*, 147, 4178 (1991)). Lastly, in a model of contact hypersensitivity, peptides Gly-Arg-Gly-Asp-Ser-Pro or Glu-Ile-Leu-Asp-Val block ear swelling when administered with sensitized cells into a challenged naive recipient mouse suggesting that $\alpha_4\beta_1$ and possibly $\alpha_5\beta_1$ are involved in this inflammatory response (Ferguson et al., *Proc. Natl. Acad. Sci. USA*, 88, 8072 (1991)). Compounds which interact with the $\alpha_4\beta_1$ and $\alpha_4\beta_7$ receptors are described in PCT Publication No. WO 94/15958. However, this publication does not describe that any of the compounds described therein inhibit $\beta_1$ and $\beta_2$ integrin-mediated adhesion.

$\beta_2$ integrins and ICAM have been shown to have important roles in graft rejection, ischemia reperfusion, delayed type hypersensitivity, asthma and allergies, inflammatory bowel disease, rheumatoid arthritis and AIDS. Support for the importance of $\beta_2$ integrins in mediating inflammatory responses has been demonstrated by the ability of monoclonal antibodies which recognize LFA-1 to block CTL-mediated lysis of target cells, as well as inhibit proliferation of T cells in response to soluble antigens, alloantigens and mitogen.

Several in vivo models have demonstrated the importance of $\beta_2$ integrins in delayed-type hypersensitivity. Anti-LFA-1 antibodies have been shown to block the migration of spleen T cells to sites of dermal inflammation, as well as the homing of lymph node and spleen T cells to peripheral and mesenteric lymph node in rats; Issekutz, T. B., *J. Immunol.*, 149, 3394–3402 (1992). Both anti-LFA-1 and anti-ICAM-1 antibodies can reduce ear swelling caused by edema and cell infiltration in association with delayed-type hypersensitivity; Scheynius, A. et al, *J. Immunol.*, 150, 655–663 (1993).

The role of $\beta_2$ integrins in allograft rejection has been demonstrated by the ability of anti-ICAM-1 antibodies to control allograft rejection and reperfusion injury in humans; Cosimi, A. B. et al, *J. Immunol.*, 144, 4604–4612 (1990); Haug et al, *Transplantation*, 55, 766–773 (1993).

Anti-ICAM-1 antibodies have also been shown to attenuate airway eosinophilia, hyper-responsiveness and asthma symptoms in a primate asthma model.

Importantly, it has been demonstrated in vivo that while either anti-$\alpha_4\beta_1$ or anti-LFA-1 antibodies alone demonstrate inhibition of delayed-type hypersensitivity-induced inflammation, a maximal anti-inflammatory response is obtained when anti-$\alpha_4\beta_1$ and anti-LFA-1 antibodies are used in combination; Issekutz, T. B., *Amer. J. Path.*, 143, 1286–1293 (1993).

As both multiple integrin/"CAM" interactions play important roles in the adhesion of leukocytes to endothelium in the inflammatory process, an ideal treatment for inflammatory disease would target both types of integrin/endothelial cell interactions.

SUMMARY OF THE INVENTION

One objective of the present invention is to provide compounds which act to modulate cell adhesion. These compounds are represented by the formula (I):

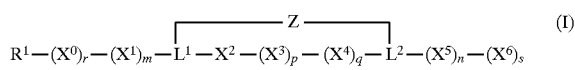

or a pharmaceutically acceptable salt thereof, wherein $L^1$ is a residue of an amino acid or an amino acid mimetic, having a functional group suitable for the formation of a cyclizing bridge, Z, between $L^1$ and $L^2$. $L^2$ is a residue of an amino acid or an amino acid mimetic, having a functional group suitable for the formation of a cyclizing bridge, Z, between $L^1$ and $L^2$. Z is a cyclizing moiety or bond between $L^1$ and $L^2$; $X^0$ is a residue of an amino acid or an amino acid mimetic and r is an integer of 0 or 1. $X^1$ is a residue of an amino acid or an amino acid mimetic and m is an integer of 0, 1 or 2. $X^2$ is $\beta$-Asp or $\gamma$-Glu or an ester or an amide derivative formed from the $\alpha$-carboxyl group of any of the aforementioned groups. $X^3$ is Ser($R^4$), Thr($R^4$), Tyr($R^4$), Ala, Gly, Lys($R^4$), Orn($R^4$), Dpr($R^4$), N-Me-Ala, Aib, Val, Tic, o- or m- halo-Tyr, dihalo-Tyr, p-halo-Phe, dihalo-Phe, Sar, Leu, Ile, Nle or Cys($R^4$) wherein when $X^3$ is Ser($R^4$), Thr($R^4$) or Tyr($R^4$), then $R^4$ is a substituent of the side chain hydroxyl group of $X^3$ and is selected from the group consisting of a hydrogen atom, a lower alkyl, a cycloalkyl, a cycloalkyl-lower alkanoyl, an aryl, an arylalkyl, an aryloxycarbonyl, an arylcarbonyl, a heteroaryl-lower alkyl, an arylacetyl, a heterocyclic group, a lower alkanoyl, and arylalkoxycarbonyl, when $X^3$ is Lys($R^4$), Orn($R^4$) or Dpr($R^4$), then $R^4$ is a substituent of the side chain terminal amino group of $X^3$ and is selected from the group consisting of a hydrogen atom, a lower alkyl, a cycloalkyl, a lower alkanoyl, an arylalkyl, an arylalkoxycarbonyl, an aryl, an aryloxycarbonyl, an arylcarbonyl, an arylacetyl, and a cycloalkyl-lower alkanoyl, when $X^3$ is Cys($R^4$), then $R^4$ is a substituent of the side chain sulfhydryl group of $X^3$ and is selected from the group consisting of a hydrogen atom, lower alkyl, an arylalkyl, an aryl, a cycloalkyl, an aryloxycarbonyl, an arylcarbonyl, an acetamido-lower alkyl, an arylacetyl, a heterocyclic group, lower alkanoyl, an arylalkoxycarbonyl and a cycloalkyl-lower alkanoyl. p is an integer of 0 or 1. $X^4$ is Pro, ThioP, Aib, TTC, Asn, TCA, Sar, N-Me-Ala and other N-methylated natural amino acids, Tic or pipecolinic acid (homoproline). q is an integer of 0 or 1. $X^5$ is a residue of an amino acid or an amino acid mimetic, n is an integer of 0, 1, 2 or 3. $X^6$ is a residue of an amino acid or an amino acid mimetic. s is an integer of 0 or 1. $R^1$ is a hydrogen atom, Xan, Fmoc, 9-FAc, 9-FCA, 1-FCA, Ac, 2-NaphAc, Ada, 5-Finc, biotinyl, Su, 1-NaphCA, For, 1-NaphAc, PhAc, 1-NaphSO$_2$, 2-NaphSO$_2$ or 2-NaphCA, with the proviso that the compound (Fmoc)-Arg-Cys*-($\beta$-Asp)-(ThioP)-Cys* is not included.

Another objective of the present invention is to provide a method for modulating cell adhesion.

Another objective of the present invention is to provide compounds which bind to a cell adhesion molecule or integrin receptor.

Another objective of the present invention is to provide compounds having high potency in modulating specific cell adhesion to integrin receptors, including inhibition of cell adhesion to ligands for both $\beta_1$ and $\beta_2$ integrins. Thus, in one regard, the present invention includes compounds having an IC$_{50}$ of less than about 500 $\mu$M as established in JY-Endothelial cell and Jurkat-Endothelial cell adhesion assays; in another regard, the invention includes compounds having an IC$_{50}$ of less than about 100 $\mu$M in such assays. The invention also includes methods for obtaining (either in vitro or in vivo), such integrin receptor adhesion inhibition. The compounds of the present invention accomplish strong inhibition at low concentrations, with an IC$_{50}$ of less than about 500 $\mu$M, or alternatively less than about 100 $\mu$M.

Another objective of the present invention is to provide compounds having high potency in modulating leukocyte adhesion to endothelial cells. Thus, in one regard, the present invention includes compounds having an IC$_{50}$ of less than about 200 $\mu$M as established in Jurkat-endothelial cell and JY-endothelial cell adhesion assays. Compounds with activity below 100 $\mu$M are most preferred, below 150 $\mu$M are preferred, below 500 $\mu$M are less preferred and above 500 $\mu$M least preferred. The invention also includes methods for obtaining (either in vitro or in vivo) such leukocyte receptor adhesion inhibition. The compounds of the present invention accomplish strong inhibition at low concentrations, with an IC$_{50}$ of less than about 250 $\mu$M.

Another objective of the present invention is to provide compounds, pharmaceutical compositions, and methods which may be used in the study, diagnosis, treatment or prevention of diseases and conditions which involve or relate to cell adhesion.

Another objective of the present invention is to provide compounds, pharmaceutical compositions and methods of treatment which may be used to inhibit inflammatory diseases in humans.

Another objective is to provide antibodies made by using the compounds of the invention, such as, but not limited to, antibodies to the compounds and anti-idiotype antibodies to the antibodies disclosed in order to study, diagnose, treat or prevent the above mentioned diseases and conditions which relate to cell adhesion.

Another objective of the present invention is to provide a matrix which can be used to purify proteins, polysaccharides or other compounds which specifically bind to the cyclic peptides of the present invention with high affinity.

The present invention relates to compounds meeting one or more of the above objectives. The compounds have activity as cell adhesion modulators. The novel compounds have been found to modulate cell adhesion by competing, for example, with integrin specific ligands, such as but not limited to, ICAM-1 and VCAM, which are sufficiently inhibited from binding to the leukocyte receptors so as to prevent or reduce cell-cell adhesion. Other uses for the compounds include enhancing cell adhesion to a distinct surface. These useful compounds can function as both cell-adhesion agonists and antagonists.

DETAILED DESCRIPTION OF THE INVENTION

The following detailed description, including those compounds exemplified herein, is provided to aid those wishing to practice the present invention. The practice of the present invention is not, however, limited to those exemplified compounds.

Cell adhesion is required for certain normal physiological functions. Yet, there are situations in which cell adhesion is undesirable, or in which modulated cell adhesion is desirable. Many pathologies exist which are related to abnormal cellular adhesion. These include, but are not limited to, rheumatoid arthritis, asthma and allergies, adult respiratory distress syndrome (ARDS), AIDS, cardiovascular disease thrombosis or harmful platelet aggregation, reocclusion following thrombolysis, allograft rejection, reperfusion injury, psoriasis, eczema, contact dermatitis and other skin inflammatory diseases, osteoporosis, osteoarthritis, atherosclerosis, neoplastic disease including metastasis of neoplastic or cancerous growth, treatment of certain eye diseases such as detaching retina, Type I diabetes, multiple sclerosis, systemic lupus erythematosus (SLE), inflammatory and immunoinflammatory conditions including ophthalmic inflammatory conditions and inflammatory bowel disease (e.g., ulcerative colitis and regional enteritis), and other autoimmune diseases.

Altered leukocyte-endothelial interactions are implicated in a number of inflammatory diseases where inappropriate attachment of leukocytes leads to further injury of affected tissue. In vitro results show that such detrimental attachment, in which the leukocyte adheres to endothelial cells or to the extracellular matrix, is mediated by integrin receptors on the leukocyte. In this situation, peptides or other compounds with a binding affinity to integrin receptors are desirable as competitive antagonists and will be useful in treating inflammatory diseases including ARDS, asthma and rheumatoid arthritis.

When insufficient cell adhesion occurs wound healing is undesirably prolonged. A peptide or other compound with suitable affinity for integrin receptors when attached, for example, to a suitably positioned matrix or surface, may be able to promote beneficial cell adhesion and resultant enhancement of wound healing.

Cell adhesion also contributes to metastasis of cancerous tumors. Metastasis has been called "the major underlying cause of death from cancer." (Welch, et al., *Intern. J. Cancer*, 43, 449 (1989)). EEV-transformed cells have been shown to have increased levels of ICAM-1 expression (Dustin et al., *J. Immunol.*, 137, 245 (1986)). Compounds which can modulate integrin mediated adhesion will be useful in the prevention and treatment of cancer metastases from tumors. These compounds could be included as part of a chemotherapeutic regime against tumors to prevent possible metastases from the primary tumor.

Increased ICAM and VCAM expression can be seen at post-capillary venuole sites. This increased expression has been suggested to play a role in increased risk of arterial blockage from increased cellular adhesion at these sites. Compounds which effect ICAM and VCAM interactions with integrins should be useful in treatment of this type of arterial blockage.

The cellular infiltration associated with graft rejection has been shown to correlate with an increased expression of both ICAM and VCAM expression (Koster and McGregor, *J. Exp. Med.*, 133, 400 (1971); Pelletier et al., *J. Exp. Med.*, 149, 2473 (1992)). Anti-ICAM antibodies are immunosuppressive in monkeys and aid in preventing graft rejection (Wee et al. *Trans. Proc.*, 23, 279 (1991)). Compounds, such as the ones encompassed by this invention are expected to be useful as immunosuppressives for preventing graft rejection. They should also have the advantage over antibodies of being less antigenic in vivo because of their small size and structural design.

The cell adhesion modulation compounds of the present invention are represented in part by amino acid sequence formulas wherein the individual amino acids are represented by their standard three-letter abbreviations, or alternatively, they are represented by one-letter abbreviations as indicated in the following Table of Abbreviations.

| Table of Abbreviations Amino Acids | | |
|---|---|---|
| Name | Abbreviations* | |
| Glycine | Gly | G |
| Alanine | Ala | A |
| Valine | Val | V |
| Leucine | Leu | L |
| Isoleucine | Ile | I |
| Methionine | Met | M |
| Phenylalanine | Phe | F |
| Proline | Pro | P |
| Serine | Ser | S |
| Threonine | Thr | T |
| Cysteine | Cys | C |
| Asparagine | Asn | N |
| Glutamine | Gln | Q |
| Tyrosine | Tyr | Y |
| Tryptophan | Trp | W |
| Aspartic acid | Asp | D |
| Glutamic acid | Glu | E |
| Histidine | His | H |
| Lysine | Lys | K |
| Arginine | Arg | R |

*Where such abbreviations for amino acids are used without an indication of enantiomeric structure, either the L- or D-enantiomers or a mixture of the L- or D-enantiomers may suitably be utilized.

*Where such abbreviations for amino acids are used without an indication of enantiomeric structure, either the L- or D-enantiomers or a mixture of the L- or D-enantiomers may suitably be utilized.

Amino acids of the peptide backbone are delineated with hyphens; synthetic amino acids, unnatural amino acids, and amino acid mimetics are enclosed in parentheses; the $R^1$–$R^5$ groups which are attached to the backbone amino acid groups are enclosed in parentheses and are immediately adjacent to the amino acid to which they are attached without an intervening hyphen.

Additional abbreviations used herein include the following:
Ac: Acetyl
Abu: 4-Aminobutyric acid
Acm: Acetamidomethyl
Ada: 1-adamantylacetyl
NH-Ada: 1-adamantylamino
Aib: α-aminoisobutyric acid
β-Ala: β-alanine (3-aminopropionic acid)
β-Asp: β-aspartic acid
AnC: 6-aminocaproic acid
ARDS: Adult Respiratory Distress Syndrome
BCECF-AM: 2', 7'-bis-(2-carboxyethyl)-5-(and -6)-carboxyfluorescein, acetoxymethyl ester, Molecular Probes Cat. No. B-1170
Biotinyl: [3aS-(3aα, 4β, 6aα)]-5-[Hexahydro-2-oxo-1H-thieno[3,4-d]imidazol-4-yl]valeryl
Boc: tert-butoxycarbonyl
BSA: bovine serum albumin
Cha: 3-Cyclohexyl-2-aminopropionic acid
CHAc: cyclohexylacetyl
CTL: cytotoxic T-lymphocyte DCC: dicyclohexylcarbodiimide
DCM: dichloromethane
DIEA: diisopropylethylamine
DMAP: p-dimethylaminopyridine
DMF: dimethylformamide
Dpr: 2,3-diaminopropionic acid
9-FAc: 9-Fluorenylacetyl
1-FCA: 1-Fluorenecarbonyl
9-FCA: 9-Fluorenecarbonyl
5-Finc: 5-Fluoroindole-2-carbonyl
Fm: 9-Fluorenylmethyl
Fmoc: 9-Fluorenylmethoxycarbonyl
FN: fibronectin
For: Formyl
γ-Glu: γ-Glutamic acid
HBSS: Hank's Buffered Saline Solution
HF: hydrofluoric acid
HOAc: acetic acid
HSA: human serum albumin
HUVEC: human umbilical vein endothelial cell
ICAM: intercellular adhesion molecule
$IC_{50}$: inhibitory concentration, concentration at which adhesion is inhibited to 50% of control level
IL-1: interleukin 1
LFA-1: Lymphocyte Functional Antigen-1
Me: methyl
MeOH: methanol
N-Me-Ala: N-methylalanine
Nα-Me-Arg: Nα-methylarginine
1-Nal: 1-Naphthylalanine[2-amino-3-(1-naphthyl) propionic acid]
2-Nal: 2-Naphthylalanine[2-amino-3-(2-naphthyl) propionic acid]
1-NaphAc: 1-Naphthylacetyl
2-NaphAc: 2-Naphthylacetyl
1-NaphCA: 1-Naphthalenecarbonyl
2-NaphCA: 2-Naphthalenecarbonyl
1-NaphSO$_2$: 1-Naphthalenesulfonyl
2-NaphSO$_2$: 2-Naphthalenesulfonyl
Nle: Norleucine
NorArg: Norarginine
  ($H_2NC(=NH)NH(CH_2)_2CH(NH_2)CO_2H$)
NorVal: Norvaline
Orn: Ornithine
PBS: phosphate buffered saline
Pen: penicillamine
  (β,β-dimethylcysteine)
PhAc: Phenylacetyl
PMA: phorbol myristate acetate
R.T.: room temperature (about 24° C.)
rTNF: recombinant Tumor Necrosis Factor
Sar: sarcosine
Ser(OMe): O-methylserine
SLE: systemic lupus erythematosus
Su: succinyl
TCA: 3-Thiomorpholinecarboxylic acid (Tetrahydro-1,4-thiazine-3-carboxylic acid)
TFA: trifluoroacetic acid
ThioP: Thioproline(4-Thiazolidinecarboxylic acid)
Thr(OMe): O-methylthreonine
Tic: 1,2,3,4-tetrahydroisoquinoline-3-carboxylic acid
TNF: Tumor Necrosis Factor
TTC: Tetrahydro-1,3-thiazine-4-carboxylic acid
Tyr(OMe): O-methyltyrosine
VCAM: vascular cell adhesion molecule
VLA: very late activation antigens
Xan: Xanthene-9-carbonyl

*: indicates participation of the amino acid in the cyclizing linkage

The chemical structures of some of the above compounds and groups are shown below.

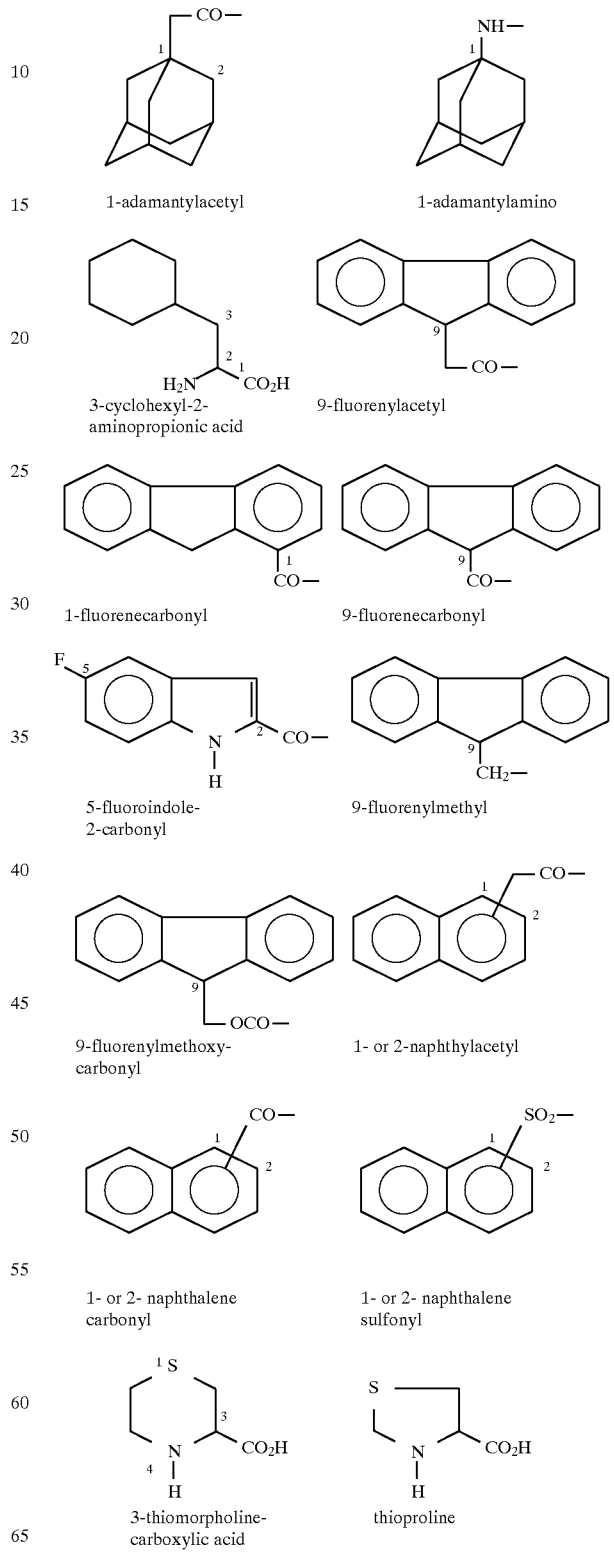

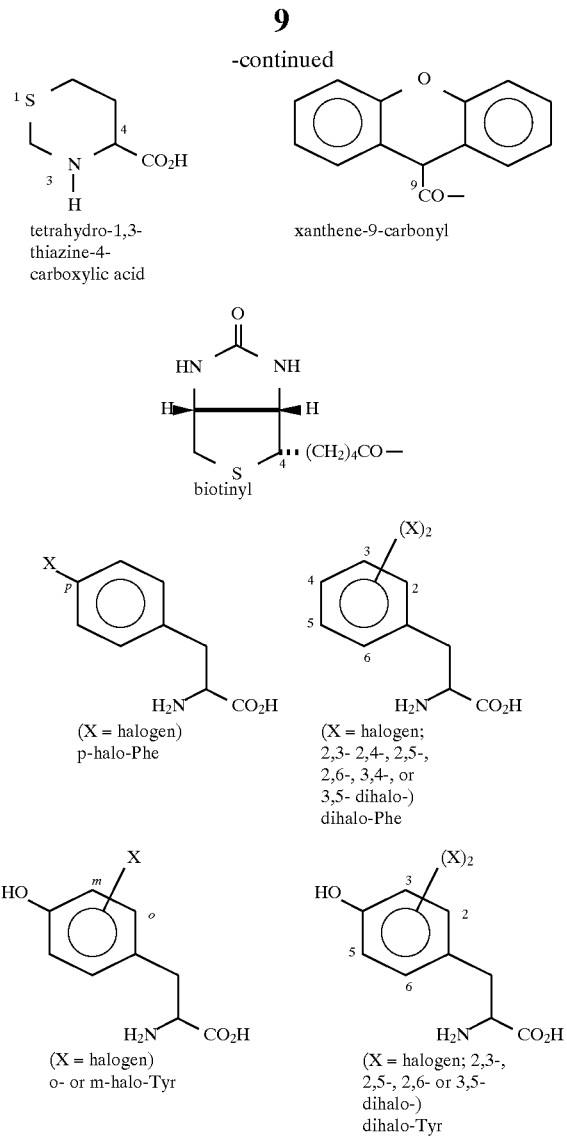

A. Description of the Compounds

As discussed above, the present invention is directed to a compound of the formula (I)

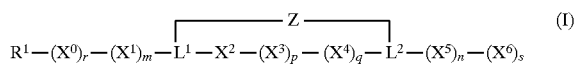

In the formula (I), $R^1$ is a substituent on the α-amino terminal group of the N-terminal amino acid. $R^1$ is preferably a hydrogen atom, Ada, 1- or 2-NaphAc, 1-NaphSO$_2$, 2-NaphSO$_2$, 1-NaphCA, 2-NaphCA, 9-FAc, 1-FCA, 9-FCA, PhAc, Ac, Fmoc, Xan, 5-Finc, biotinyl, Su and For.

In formula (I), $X^0$ is an optional group, r is an integer of 0 or 1, and when present, $X^0$ is preferably Trp, 1-Nal, 2-Nal, or an aromatic or hydrophobic amino acid, such as Tyr, Leu, Nle, Ile, Val, NorVal and Cha.

In formula (I), $X^1$ is an optional group, "m" is an integer of 0, 1 or 2 and when present, $X^1$ is preferably a hydrophobic amino acid or a side chain-protected basic amino acid residue having a side chain terminal amino group with the formula —NHR$^2$, where $R^2$ is selected from the group consisting of a hydrogen atom, PhAc, 1-NaphAc, 2-NaphAc, Ada, 2-norbornylacetyl, 1-FCA, CHAc and For.

Preferred moieties for $X^1$ include Arg, Lys(R$^2$), Gly, Nα-Me-Arg, Nle, Cha, Orn(R$^2$), Val, NorVal, Dpr(R$^2$), Abu, Leu and Ile.

In formula (I), $X^2$ is selected from D- and L-β-Asp and D- and L-γ-Glu and α-carboxyl esters or amides of any of these aforementioned amino acids. The carboxyl peptide linkages of β-Asp and γ-Glu are formed between the side chain carboxyl groups (β-carboxyl or γ-carboxyl) of β-Asp and γ-Glu, respectively, and the α-amino group of the adjacent amino acid. The α-carboxyl group of $X^2$ may have the formula —C(O)R$^3$, where R$^3$ is —OR, —NHR or —NRR and where R is a hydrogen atom, a lower alkyl, an aryl, an arylalkyl, a cycloalkyl, a heteroaryl-lower alkyl or a heterocyclic group as appropriate for an amide or ester. More specifically, R may be methyl, Fm, benzyl, cyclohexyl, 1-adamantyl, 2-, 3- or 4-picolyl, 1- or 2-naphthylmethyl or isobutyl. When R$^3$ is —OR and R is a hydrogen atom, —C(O)OH is present. Where R$^3$ is —NHR or —NRR and R is a hydrogen atom, a carboxamide is present. Otherwise, for —NRR each R group may be selected independently of the other R group.

In formula (I), $X^3$ is an optional amino acid residue where "p" is an integer of 0 or 1. When present, preferred amino acids include Ser(R$^4$), Thr(R$^4$), Tyr(R$^4$), Ala, Gly, Lys(R$^4$), Orn(R$^4$), Dpr(R$^4$), N-Me-Ala, Aib, Val, Tic, o- and m-halo-Tyr, dihalo-Tyr, p-halo-Phe, dihalo-Phe, Sar, Leu, Ile, Nle and Cys(R$^4$).

In formula (I), $X^4$ is an optional amino acid, where "q" is an integer of 0 or 1. When present, preferred amino acids include Pro, ThioP, Aib, Asn, TCA, TTC, Sar, N-Me-Ala, other N-methylated natural amino acids, Tic and pipecolinic acid (homoproline).

In formula (I), $X^5$ is optional and "n" is an integer of 0, 1, 2 or 3. In formula (I), $X^6$ is optional and "s" is an integer of 0 or 1. Preferred groups for $X^5$ and/or $X^6$ include a side chain-protected derivative of a basic amino acid residue having a side chain terminal amino group with the formula —NHR$^4$; a side chain-protected derivative of an acidic amino acid residue having a side chain terminal carboxyl group with the formula —C(O)R$^4$, where R$^4$ is —OR, —NHR or —NRR; Ser(R$^4$), Thr(R$^4$), Tyr(R$^4$), and R$^4$ is a substituent of the hydroxyl group; and Cys(R$^4$) and R$^4$ is a substituent of the sulfhydryl group. Other preferred groups for $X^5$ and/or $X^6$ include Ala; Asp(R$^4$); Glu(R$^4$); Ser(OMe); Thr(OMe); Tyr(OMe); Gly; Abu; AnC; Leu; Val; β-Ala; Lys(R$^4$); Dpr(R$^4$); Orn(R$^4$), Ile and Nle.

On $X^3$, $X^5$ or $X^6$, R$^4$ is a substituent of a terminal amino group of a side chain of a basic amino acid, of a β- or γ-carboxylic group of an acidic amino acid, of a side chain hydroxyl group of Ser, Thr, Tyr or of a hydroxyl containing derivative or analog of Ser, Thr or Tyr or of a sulfhydryl group of Cys or of a sulfhydryl containing derivative or analog of Cys.

When $X^5$ and/or $X^6$ is a residue of an acidic amino acid or mimetic thereof, the terminus of the side chain may be represented by the formula —C(O)R$^4$ and R$^4$ is —OR, —NHR or —NRR, wherein R may be a hydrogen atom, a lower alkyl, an aryl, an arylalkyl, a cycloalkyl, a heteroaryl-lower alkyl or a heterocyclic group as is appropriate for an amide or ester functional group. More specifically, R may be benzyl, cyclohexyl, 1- or 2-naphthylmethyl, 2-, 3- or 4-picolyl, 1-adamantyl, Fm, isobutyl or methyl. Where R$^4$ is —OR and R is H, the side chain terminal functionality —C(O)OH, is present. Where R$^4$ is NHR or NRR and R is H, a carboxamide is present. Otherwise, for —NRR, each R group may be selected independently of the other R group.

When $X^3$, $X^5$ or $X^6$ is Ser($R^4$), Thr($R^4$) or Tyr($R^4$), $R^4$ is a substituent of the hydroxyl group and may be a hydrogen atom, a lower alkyl, a cycloalkyl, a cycloalkyl-lower alkanoyl, an aryl, an arylalkyl, an aryloxycarbonyl, an arylcarbonyl, a heteroaryl-lower alkyl, an arylacetyl, a heterocyclic group, a lower alkanoyl, or an arylalkoxycarbonyl. More specifically, $R^4$ may be methyl, benzyl, cyclohexyl, 1- or 2-naphthylmethyl, Fm, 2-, 3- or 4-picolyl or isobutyl. If $R^4$ is a hydrogen atom, a hydroxyl side chain is present.

When $X^3$, $X^5$ or $X^6$ is a residue of a basic amino acid, the terminal group of the side chain may be denoted by the formula —$NHR^4$. Preferred groups for $R^4$ include a hydrogen atom, lower alkyl, aryl, aryloxycarbonyl, arylcarbonyl, arylacetyl, an arylalkyl, an arylalkoxycarbonyl, a lower alkanoyl, cycloalkyl, and cycloalkyl-lower alkanoyl. More specifically, $R^4$ may be cyclohexyl, 1- and 2-naphthylmethyl, Fmoc, 1-FCA, 9-FCA, Ada, Ac and 9-FAc. When $R^4$ is a hydrogen atom, an amino terminus of the side chain is present.

When $X^3$, $X^5$ or $X^6$ is Cys($R^4$) or a sulfhydryl side chain-containing analog or derivative of Cys, $R^4$ is a substituent of the sulfhydryl group and is a hydrogen atom, a lower alkyl, an arylalkyl, an aryl, a cycloalkyl, a cycloalkyl-lower alkanoyl, an aryloxycarbonyl, an arylcarbonyl, an acetamido-lower alkyl, an arylacetyl, a heterocyclic group, a lower alkanoyl, or an arylalkoxycarbonyl. More specifically, $R^4$ is preferably methyl, benzyl, 1- or 2-naphthylmethyl, cyclohexyl, Fm, Acm, 4-methylbenzyl or Ada. $R^4$ is preferably not a hydrogen atom; however, where $R^4$ is a hydrogen atom, a sulfhydryl terminal group of the side chain is present.

When $X^5$ and/or $X^6$ is the C-terminal amino acid residue, the $\alpha$-carboxyl group may be represented by the formula —C(O)$R^5$, where $R_5$ is —OR, —NHR, or —NRR and R is a hydrogen atom, a lower alkyl, an arylalkyl, an aryl, a cycloalkyl, a heteroaryl-lower alkyl or a heterocyclic group as is appropriate for an amide or ester functional group. More specifically, R may be methyl, Fm, isobutyl, benzyl, cyclohexyl, 1- or 2-naphthylmethyl, 1-adamantyl or 2-, 3- or 4-picolyl. If $R_5$ is —OR and R is H, an $\alpha$-carboxyl terminus, —C(O)OH, is present. Where $R^5$ is —NHR or —NRR and R is H, a carboxamide is the C-terminus of the peptide. For —NRR, each R group may be selected independently of the other R group.

$R^1$–$R^5$, where present, are preferably each independently selected so as to enhance the specific activity of the resulting compound and/or to preserve the compound against metabolism in the in vivo environment and to increase the effective half-life of the compound. In this regard, the use of one or more groups for $X^0$–$X^6$, particularly at the N-terminal position or in other regions in the compound, promotes the activity of the compound.

In formula (I), a bridge is formed via a cyclizing moiety, Z, between $L^1$ and $L^2$. $L^1$ and $L^2$ are each, or together, residues of amino acids or amino acid mimetics having functional groups suitable for the formation of a cyclizing bridge between $L^1$ and $L^2$.

$L^1$ and $L^2$ are chosen so that each contains a functional group which contributes to the formation of the cyclizing bridge moiety, Z. Thus, Z is formed from functional groups contributed by $L^1$ and $L^2$ and may also contain additional atoms and spacer groups. As is discussed in more detail below, preferred functional groups include thiol, amino and carboxyl groups. Such functional groups may be borne on the side chain of amino acids or amino acid mimetics, or may constitute the $\alpha$-amino group (in $L^1$) or terminal-carboxyl group (in $L^2$) thereof.

Preferred moieties for $L^1$ and $L^2$ are Cys, Cys—$NH_2$ (only for $L^2$ and when no $X^5$ or $X^6$ groups are present), Arg (only for $L^1$ and when $X^0$ or $X^1$ are absent), Pen, Orn, Lys, Dpr, Gly (only for $L^1$ and when $X^0$ or $X^1$ are absent), Met, Glu and Asp.

In preferred embodiments of the invention, $L^1$ and $L^2$ are each selected from Cys or Pen. Both Cys and Pen contain a sulfhydryl group and thus, the bridging cyclization can be accomplished by oxidative coupling of the sulfhydryls to form a disulfide bond between residues $L^1$ and $L^2$. In such a case, the cyclizing moiety, Z, is a covalent bond between the two sulfur atoms. This may be depicted generally for compounds wherein, both $L^1$ and $L^2$ are Cys residues as follows:

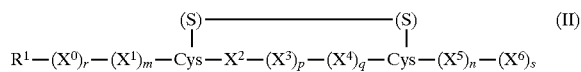

wherein (as with other similar depictions used herein) the functional group portion (here a side chain sulfur atom in both instances) appears in parentheses above the residue having the functional group.

Particularly preferred embodiments are those where $L^1$ is Cys and $L^2$ is Cys.

The cyclizing moiety may also be formed by a hydrocarbon moiety, for example a (poly)methylene bridge moiety of the form —$(CH_2)_y$— where y is an integer from 1 to 8, preferably 1 to 4. One type of such a bridge is represented below, wherein a cyclic compound is formed with methylene residues, representing Z, between two cysteine side-chain sulfur atoms (representing $L^1$ and $L^2$). (See, L. Fieser et al., "Reagents for Organic Synthesis", Vol. 1, pp. 356–357, J. Wiley and Sons: (1967); Fieser, *J. Amer. Chem. Soc.*, 96, 1945 (1959)).

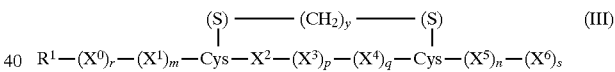

In another preferred embodiment, $L^1$ and $L^2$ may be chosen from other natural or synthetic, L- or D-amino acids or amino acid mimetics which provide a side chain or an amino- or carboxyl-terminus suitable as a functional group, for the formation of a cyclizing moiety. For example, $L^2$ may be selected from Asp, Glu, or other natural or synthetic amino acids which provide a suitable side chain carboxyl group for cyclic linkage, through formation of an amide bond in a condensation reaction, with an amino group (e.g., an N$\alpha$-amino group, or an $\omega$ side chain amino group as on, for example, Lys or Orn) on $L^1$. The cyclizing moiety Z may be a simple amide bond between $L^1$ and $L^2$.

Or, an amino acid residue $L^2$ may provide an $\alpha$-carboxyl group from its carboxyl terminus for amide linkage with either a side chain amino or $\alpha$-amino group on $L^1$; the direction of the amide linkage may also be reversed where $L^1$ provides a side chain carboxyl group and $L^2$ provides a side chain amino group. Such structures are exemplified as follows:

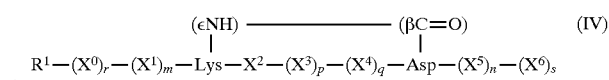

wherein the side chain amino and carbonyl groups of $L^1$ (Lys) and $L^2$ (Asp) are directly bonded (IV);

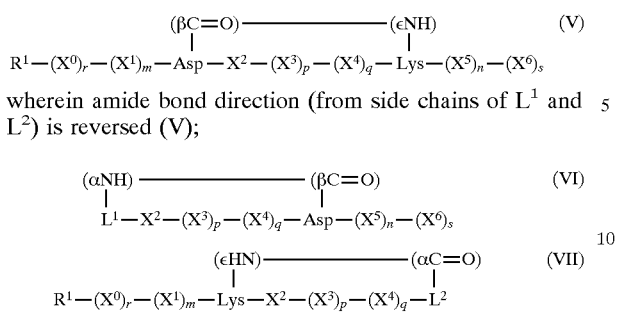

wherein amide bond direction (from side chains of $L^1$ and $L^2$) is reversed (V);

wherein the depicted amino terminus of $L^1$ is directly bonded to the side chain carboxyl group of Asp ($L^2$) (VI), or the depicted α-carboxyl terminus of $L^2$ is directly bonded to the side chain amino group of Lys ($L^1$) (VII);

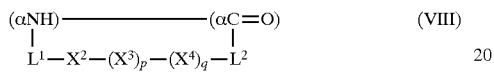

wherein the depicted a-amino terminus at $L^1$ is directly bonded to the depicted carboxyl terminus at $L^2$, such that an amide bond is formed in the peptide "backbone" of the compound (VIII).

The cyclizing bridge between $L^1$ and $L^2$ may also be formed via a monosulfide (thioether) linkage, as exemplified below. In this regard, see, Palmer et al., in "Peptides—Chemistry, Structure, Biology", pp. 616–618, Rivier & Marshall, Ed., Escom. Leider (1990); and Jung, op. cit., pp. 865–869.

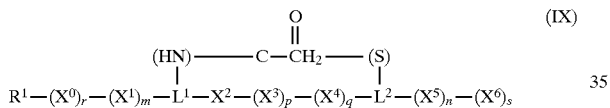

If $L^2$ is the C-terminal amino acid of the compound and the α-carboxyl group is not utilized in the cyclization of the compound, the α-carboxyl group may be represented as —C(O)$R^5$ where $R^5$ is —OR, —NHR or —NRR and R is H, a lower alkyl, an aryl, an arylalkyl, a cycloalkyl, a heteroaryl-lower alkyl or a heterocyclic group as is appropriate for an amide or ester functional group. More specifically, R may be methyl, benzyl, cyclohexyl, 1- or 2-naphthylmethyl, 1-adamantyl, Fm, 2-, 3- or 4-picolyl or isobutyl. If $R^5$ is —OR and R is H, the α-carboxyl group, —C(O)OH, is present on $L^2$. Where $R^5$ is —NHR or —NRR and R is H, the carboxamide is present. Otherwise, each R group in —NRR may be selected independently of the other R group.

Other means of cyclization through appropriate choices of $L^1$, $L^2$ and Z will be readily recognized by those of ordinary skill in the art and are included in the scope of the present invention. Synthetic amino acid residues may also be utilized for $L^1$ or $L^2$, as for example, homologues wherein a side chain is lengthened or shortened while still providing the sulfhydryl carboxyl, amino or other reactive functional group for cyclization.

The foregoing discussion of cyclizing moieties (Z) bridging residues ($L^1$ and $L^2$), substituents, synthetic amino acids, amino acid mimetics, cyclization methods, and the like are applicable to the other structural formulas discussed hereinafter.

The preferable compounds are compounds of the formula (I) wherein $L^1$ and $L^2$ are each or together selected from the group consisting of Cys, Cys—$NH_2$ (only for $L^2$ and when no $X^5$ or $X^6$ groups are present), Arg (only for $L^1$ and when $X^0$ and $X^1$ are absent) Pen, Orn, Lys, Dpr, Gly (only for $L^1$ and when $X^0$ and $X^1$ are absent), Met, Glu and Asp;

Z is selected from a single bond, a lower alkylene or formula: —$COCH_2$—;

$X^0$ is selected from the group consisting of Trp, 1-Nal, 2-Nal, Tyr, Leu, Nle, Ile, Val, NorVal and Cha;

$X^1$ is selected from the group consisting of Lys($R^2$) Gly, Nα-Me-Arg, Nle, Cha, Val, NorVal, Dpr($R^2$), Arg, Orn($R^2$), Leu, Ile and Abu;

$R^2$ is selected from a hydrogen atom, Ada, 2-norbornylacetyl, 1-FCA, 1-NaphAc, 2-NaphAc, PhAc, For or CHAc;

$X^2$ is selected from the group consisting of β-Asp and β-Asp($R^3$), γ-Glu and γ-Glu($R^3$) and $R^3$ is —OR, —NHR or —NRR and where R is a hydrogen atom, a lower alkyl, an aryl, an arylalkyl, a cycloalkyl, a heteroaryl-lower alkyl or a heterocyclic group; and $X^5$ and/or $X^6$ is selected from the group consisting of Ala; Asp($R^4$) and Glu($R^4$) wherein $R^4$ is a substituent of the derivatized side chain terminal carboxyl group and is selected from the group consisting of —OR, —NRR and —NHR where R is selected from the group consisting of a hydrogen atom, a lower alkyl, an aryl, a cycloalkyl, a heteroaryl-lower alkyl, a heterocyclic group and an arylalkyl; Ser($R^4$), Tyr($R^4$) and Thr($R^4$) wherein $R^4$ is OR and R is selected from the group consisting of a hydrogen atom, a lower alkyl, a cycloalkyl, an aryl, an arylalkyl, a cycloalkyl-lower alkanoyl, an aryloxycarbonyl, an arylcarbonyl, a heteroaryl-lower alkyl, an arylacetyl, a heterocyclic group, a lower alkanoyl and an arylalkoxycarbonyl; Gly; Abu; Lys($R^4$); Dpr($R^4$) and Orn($R^4$) wherein $R^4$ is a substituent of the derivatized side chain terminal amino group and is selected from the group consisting of a hydrogen atom, a lower alkyl, a cycloalkyl, a lower alkanoyl, an arylalkyl, an arylalkoxycarbonyl, an aryl, an aryloxycarbonyl, an arylcarbonyl, a cycloalkyl-lower alkanoyl and an arylacetyl; AnC; Leu; Val; Ile; Nle; β-Ala and Cys($R^4$) wherein $R^4$ is a substituent of the derivatized side chain sulfhydryl group expressed as —SR and R is selected from the group consisting of a hydrogen atom, a lower alkyl, a cycloalkyl, an acetamido-lower alkyl, an aryl, an arylalkyl, an aryloxycarbonyl, an arylcarbonyl, an arylacetyl, a heterocyclic group, a lower alkanoyl, an arylalkoxycarbonyl and a cycloalkyl-lower alkanoyl.

Among the above preferable compounds, more preferable ones are those wherein $R^1$ is selected from the group consisting of hydrogen, Xan, 9-FAc, 9-FCA, 1-FCA, Ac, 2-NaphAc, Ada, 5-Finc, biotinyl, Su, 1-NaphCA, For, 1-NaphAc, PhAc, 1-Naph$SO_2$, 2-Naph$SO_2$ and 2-NaphCA.

Among the above more preferable compounds, most preferable ones are those wherein p is an integer of 1.

Other preferable compounds are compounds of the formula (I) wherein

Z is selected from a single bond, a lower alkylene or a group of the formula: —$COCH_2$—;

$R^1$ is selected from hydrogen, 1-FCA, 9-FAc, Ada, 5-Finc, Ac, Biotinyl, 9-FCA, Fmoc, For, 1- or 2-NaphAc, PhAc, 1-Naph$SO_2$, 2-Naph$SO_2$, 1- or 2-NaphCA, Xan or Su;

$X^0$ is selected from the group consisting of Trp, 1-Nal, 2-Nal, Tyr, Leu, Nle, Ile, Val, NorVal and Cha;

r is an integer of 0 or 1;

$X^1$ is selected from Arg, Nα-Me-Arg, Lys, Lys(Ada), Lys(1-NaphAC), Lys(PhAc), Lys(For), Lys(2-NaphAc), Orn, Orn(PhAc), Gly, Nle or Cha;

m is an integer of 0 or 1;

$L^1$ is selected from Cys, Lys, Pen, Orn or Dpr;

$X^2$ is selected from β-Asp or β-Asp(αOFm);

$X^3$ is selected from Ser, N-Me-Ala, Gly or Ala;

$X^4$ is selected from ThioP, Asn, TCA, Pro, Aib or Tic;

$L^2$ is selected from Cys, Cys—$NH_2$ (only when no $X^5$ or $X^6$ groups are present), Asp, Pen or Glu;

$X^5$ is selected from Ala, Gly, Abu or Lys (Fmoc); and $X^6$ is selected from Asp-(OFm), Asp-(NH-Ada), Ser, Lys, Lys(Fmoc)—$NH_2$ or Gly.

Among the above preferable compounds, more preferable ones are those wherein $R^1$ is selected from a hydrogen atom, 1-FCA, 9-FAc, Ada, 5-Finc, Ac, Biotinyl, 9-FCA, For, 9-FAc, 2-NaphAc, PhAc, 1-NaphSO$_2$, 2-NaphSO$_2$, 2-NaphCA or Xan.

Among the above more preferable compounds, most preferable ones are those wherein p is an integer of 1.

Other preferable compounds are compounds of the formula (I) wherein

Z is selected from a single bond, a lower alkylene or a group of the formula: —COCH$_2$—;

$R^1$ is selected from hydrogen, 1-FCA, 9-FAc, Ada, 5-Finc, Ac, Biotinyl, 9-FCA, Fmoc, For, 9-FAc, 2-NaphAc, PhAc, 2-NaphCA or Xan;

$X^0$ is Trp;

r is an integer of 0 or 1;

$X^1$ is selected from Arg, Nα-Me-Arg, Lys, Lys(Ada), Lys(1-NaphAc), Lys(PhAc), Lys(For), Lys(2-NaphAc), Orn, Orn(PhAc), Gly, Nle or Cha;

m is an integer of 0 or 1;

$L^1$ is selected from Cys, Lys or Pen;

$X^2$ is β-Asp;

$X^3$ is selected from Gly or Ala;

$X^4$ is selected from ThioP, Asn, Pro or Tic;

$L^2$ is selected from Cys, Cys—$NH_2$ (only when no $X^5$ or $X^6$ groups are present), Asp or Pen;

$X^5$ is selected from Ala, Gly, Abu or Lys(Fmoc); and $X^6$ is selected from Asp-(OFm), Asp-(NH-Ada), Ser, Lys, Lys(Fmoc)—$NH_2$ or Gly.

Among the above preferable compounds, more preferable ones are those wherein $R^1$ is selected from a hydrogen atom, 1-FCA, 9-FAc, Ada, 5-Finc, Ac, Biotinyl, 9-FCA, For, 9-FAc, 2-NaphAc, PhAc, 1-NaphSO$_2$, 2-NaphSO$_2$, 2-NaphCA or Xan.

Among the above more preferable compounds, most preferable ones are those wherein p is an integer of 1.

Other preferable compounds are compounds of the formula (I) wherein

Z is a single bond;

$R^1$ is selected from 1-FCA, 9-FAc, Ac or Xan;

r is an integer of 0;

$X^1$ is selected from Arg or Lys;

m is an integer of 1;

$L^1$ is Cys;

$X^2$ is β-Asp;

p is an integer of 0;

$X^4$ is ThioP;

q is an integer of 1;

$L^2$ is selected from Cys or Cys—$NH_2$ (only when no $X^5$ or $X^6$ groups are present);

n is an integer of 0; and s is an integer of 0.

Within a preferred group of structures are the following formulas:

$X^0$ in structure I is absent; $X^1$ is Arg; $X^2$ is β-Asp; $X^3$ is absent; $X^4$ is ThioP; and $X^5$ and $X^6$ are absent. In a preferred structure, the cyclizing Z moiety is formed by a disulfide linkage between $L^1$ and $L^2$ cysteine residues and the overall preferred sequence would be Arg-Cys*-(β-Asp)-(ThioP)-Cys* (* denotes residue involved in cyclization of compound).

With the sequence Arg-Cys*-(β-Asp)-(ThioP)-Cys*, $R^1$ is preferably 1-FCA, 9-FAc, 9-FCA, Xan, For, Ac, Biotinyl, Ada, a hydrogen atom, 5-Finc, PhAc or Su.

Also preferred is a sequence wherein residue $X^0$ is absent, residue $X^1$ is Lys; residue $X^2$ is β-Asp; $X^3$ is absent; $X^4$ is ThioP; and $X^5$ and $X^6$ are absent. Thus, the sequence Lys-Cys*-(β-Asp)-(ThioP)-Cys* is also preferred, wherein the cyclizing Z moiety is formed by the disulfide linkage between the cysteine residues. In this preferred structure $R^1$ is preferably 1-FCA, 9-FCA or 9-FAc or Fmoc.

Another particularly preferred sequence is one wherein $X^0$ is absent; $X^1$ is Arg; $X^2$ is β-Asp; $X^3$ is absent; $X^4$ is ThioP; and $X^5$ is Ala, and n is 2 and $X^6$ is absent. Thus, the sequence Arg-Cys*-(β-Asp)-(ThioP)-Cys*-Ala-Ala is also preferred, wherein the cyclizing z moiety is formed by a disulfide linkage between the cysteine residues. In this preferred structure, $R^1$ is preferably 1-FCA, 9-FCA, 2-NaphAc, 1-NaphSO$_2$, 2-NaphSO$_2$, 2-NaphCA, Ac or PhAc.

Another particularly preferred sequence is one wherein $X^0$ is absent; $X^1$ is Lys; $X^2$ is β-Asp; $X^3$ is absent; $X^4$ is ThioP; $X^5$ is Ala and n is an integer of 2 and $X^6$ is absent. Thus, the sequence Lys-Cys*-(β-Asp)-(ThioP)-Cys*-Ala-Ala is also preferred, wherein the cyclization of the peptide occurs through a disulfide linkage formed between the cysteine residues. With this preferred structure, $R^1$ is preferably 9-FCA and $R^2$ is PhAc.

Another particularly preferred sequence is one wherein $X^0$ is absent; $X^1$ is Arg; $X^2$ is β-Asp; $X^3$ is absent; $X^4$ is ThioP; $X^5$ is Ala and $X^6$ is Asp. Thus, the sequence Arg-Cys*-(β-Asp)-(ThioP)-Cys*-Ala-Asp is also preferred, wherein the cyclization is formed from the disulfide linkage of the two cysteines. With this preferred structure, $R^1$ is preferably Ac and $R^4$ is Ada or Fm.

Also preferred is a sequence wherein residue $X^0$ is absent; $X^1$ is Orn; $X^2$ is β-Asp; $X^3$ is absent; $X^4$ is ThioP and $X^5$ and $X^6$ are absent. Thus, the sequence Orn-Cys*-(β-Asp)-(ThioP)-Cys* is also preferred, wherein the sulfhydryl linkages of the two cysteine residues cyclize the peptide. In this structure $R^1$ is preferably 1-FCA or Fmoc and the side chain terminal amino group of Orn is denoted as $NHR^2$, and $R^2$ is preferably hydrogen or PhlAc.

Another particularly preferred sequence is one wherein $X^0$ is absent; $X^1$ is Arg; $X^2$ is β-Asp; $X^3$ is absent; $X^4$ is ThioP; $X^5$ is Ala and $X^6$ is Ser. Thus, the sequence Arg-Cys*-(β-Asp)-(ThioP)-Cys*-Ala-Ser is also preferred, wherein the peptide is cyclized by a disulfide linkage of the cysteine residues. In this structure, $R^1$ is preferably 1-FCA.

Another particularly preferred sequence is one wherein $X^0$ is absent; $X^1$ is Lys; $X^2$ is β-Asp; $X^3$ is absent; $X^4$ is TCA; and $X^5$ and $X^6$ are absent. Thus, the sequence Lys-Cys*-(β-Asp)-(TCA)-Cys* is also preferred, wherein the peptide is cyclized by a disulfide linkage of the cysteine residues. In this structure, $R^1$ is preferably Fmoc, 9-FAc, 9-FCA or 1-FCA, the ε-amino terminal group of Lys is denoted as $NHR^2$ and $R^2$ is preferably H, 1-NaphAc, 2-NaphAc or PhAc.

Another particularly preferred sequence is one wherein $X^0$ is absent; $X^1$ is Lys; $X^2$ is β-Asp; $X^3$ is absent; $X^4$ is Pro; $X^5$ and $X^6$ are absent. Thus, the sequence Arg-Cys*-(β-Asp)-Pro-Cys* is also preferred, wherein the peptide is cyclized by a disulfide linkage of the cysteine residue. In this structure, $R^1$ is preferably Fmoc, 9-FAc, 9-FCA or 1-FCA.

Another particularly preferred sequence is one wherein $X^0$ is absent; $X^1$ is Arg; $X^2$ is β-Asp; $X^3$ is absent; $X^4$ is absent and $X^5$ and $X^6$ are absent. Thus, the sequence Arg-Cys*-(β-Asp)-Cys* is also preferred, wherein the cyclizing Z moiety is formed by a disulfide linkage between the cysteine residues. In this preferred structure, $R^1$ is preferably 1-FCA, 9-FCA, 9-FAc or Fmoc.

Another particularly preferred sequence is one wherein $X^0$ is absent; $X^1$ is Arg; $X^2$ is β-Asp; $X^3$ is absent; $X^4$ is ThioP; $X^5$ is Abu and $X^6$ is absent. Thus, the sequence Arg-Cys*-(β-Asp)-(ThioP)-Cys*-Abu is also preferred, wherein the cyclization of the peptide occurs through a disulfide linkage formed between the cysteine residues. With this preferred structure, $R^1$ is preferably 9-FCA, 1-FCA, 9-FAc or Fmoc.

Another particularly preferred sequence is one wherein $X^0$ is absent; $X^1$ is Arg; $X^2$ is β-Asp; $X^3$ is absent; $X^4$ is ThioP; $X^5$ is Ala and $X^6$ is absent. Thus, the sequence Arg-Cys*-(β-Asp)-(ThioP)-Cys*-Ala is also preferred, wherein the sulfhydryl linkages of the two cysteine residues cyclize the peptide. In this structure, $R^1$ is preferably 1-FCA.

Another particularly preferred sequence is one wherein $X^0$ is absent; $X^1$ is Arg; $X^2$ is β-Asp; $X^3$ is absent; $X^4$ is ThioP; $X^5$ is Gly and n is an integer of 2 and $X^6$ is absent. Thus, the sequence Arg-Cys*-(β-Asp)-(ThioP)-Cys*-Gly-Gly is also preferred, wherein the cyclizing Z moiety is formed from the disulfide linkage of the cysteine residues. In this structure, $R^1$ is preferably 1-FCA, 9-FCA, 9-FAc or Fmoc.

Another particularly preferred sequence is one wherein $X^0$ is absent; $X^1$ is Lys; $X^2$ is β-Asp; $X^3$ is absent; $X^4$ is ThioP; $X^5$ is Ala and $X^6$ is Ser. Thus, the sequence Lys-Cys*-(β-Asp)-(ThioP)-Cys*-Ala-Ser is also preferred, wherein the cysteine residues are joined by a disulfide linkage. In this structure, $R^1$ is preferably 1-FCA or 9-FCA, the ε-amino terminal group of Lys is denoted as $NHR^2$ and $R^2$ is preferably H, 2-NaphAc, 1-NaphAc or PhAc.

Also preferred is a sequence wherein residue $X^0$ is absent; $X^1$ is Arg; $X^2$ is β-Asp; $X^3$ is absent and $X^4$ is ThioP; $X^5$ is Ala and $X^6$ is Lys. Thus, the sequence Arg-Cys*-(β-Asp)-(ThioP)-Cys*-Ala-Lys is also preferred, wherein the cysteine residues cyclize the compound by forming a disulfide linkage. With this structure $R^1$ is preferably 2-NaphAc or 9-FAc.

Throughout the present specification and claims, amino acids are those from natural or non-natural sources and are those having at least one amino group and one carboxyl group in a molecule. Those amino acids include amino acids from natural sources or antipodes thereof, D- or L-enantiomeric amino acids, and racemic mixtures of these amino acids.

α-Amino acids or β-amino acids are the preferred examples and may be either one of neutral, acidic, and basic amino acids. As the basic amino acids, there may be mentioned amino acids having plural amino groups or a guanidino group or an imidazolyl group such as arginine, histidine, ornithine, lysine, and the like; as the acidic amino acids, there may be mentioned amino acids having plural carboxyl groups such as glutamic acid, aspartic acid, and the like; and as the neutral amino acids, there may be mentioned amino acids having the same number of amino groups and carboxyl groups such as alanine, isoleucine, leucine, and the like. Further, in the present invention, specific examples of the amino acids which can be used suitably, include glycine, alanine, N-methylalanine, N-α-methylarginine, isoleucine, leucine, valine, norvaline, glutamic acid, methionine, phenylalanine, proline, β-alanine, arginine, norarginine, ornithine, serine, O-methylserine, threonine, O-methylthreonine, asparagine, aspartic acid, β-aspartic acid, glutamine, γ-glutamine, cystine, cysteine, tyrosine, O-methyltyrosine, histidine, tryptophan, lysine, homoarginine, γ-glutamic acid, sarcosine, creatine, homocysteine, norleucine, isoserine, homoserine, norvaline, ornithine, penicillamine, sarcosine, 3-cyclohexyl-2-aminopropionic acid, 2,3-diaminopropionic acid, thioproline, piperidylcarboxylic acid, α,β-diaminobutyric acid, α-aminoisobutyric acid, β-aminobutyric acid, 4-aminobutyric acid, 6-aminocaproic acid, 1,2,3,4-tetrahydroisoquinoline-3-carboxylic acid and the like.

Amino acid mimetics are derivatives of the above amino acids. Specific examples of those which can be used suitably, include ester thereof (e.g., a lower alkyl ester, aryl ester), amide thereof (e.g., unsubstituted amide, a cyclohexylamide) or derivative of proline (e.g., thioproline, 3-thiomorpholinecarboxylic acid, tetrahydro-1,3-thiazine-4-carboxylic acid, homoproline, hydroxyproline) and the like.

An aryl group, an aryl moiety in the arylalkyl, aryloxycarbonyl, arylcarbonyl, arylacetyl or arylalkoxycarbonyl is preferably an aromatic hydrocarbocyclic group containing 1 to 4 rings, such as phenyl group, naphthyl group, and the like. A heteroaryl group is preferably an aromatic group containing 1 or 2 rings wherein at least one of the rings contains at least 1, preferably 1 to 3, more preferably 1 or 2 heteroatoms such as N, O or S wherein the remainder of the ring atoms are carbon atoms, wherein each ring contains 4 to 7 ring atoms, with a total of 4 to 11 ring atoms where two fused rings are present. For example, a heteroaryl group is a 5- or 6-membered aromatic heterocyclic group such as thienyl group, furyl group, pyridyl group, pyrazinyl group, pyrimidinyl group, and the like. The above aryl and/or heteroaryl group may have one to three substituents and as the substituent, there may be mentioned a halogen atom, a lower alkyl group and a lower alkoxy group.

As used hereinabove, a lower alkyl group is preferably a $C_1$–$C_8$ alkyl group, more preferably a $C_1$–$C_5$ alkyl group, a lower alkanoyl group is preferably a $C_1$–$C_9$ alkanoyl group, more preferably a $C_1$–$C_6$ alkanoyl group, a lower alkoxy group is preferably a $C_1$–$C_8$ alkoxy group, more preferably a $C_1$–$C_5$ alkoxy group, aryl is preferably a $C_6$–$C_{17}$ aryl group (containing 1 to 4 rings), more preferably a $C_6$–$C_{12}$ aryl group (containing 1 or 2 rings) and most preferably is an aromatic hydrocarbocyclic group containing 1 or 2 rings, such as a phenyl group, naphthyl group and the like, arylalkyl is preferably a $C_6$–$C_{17}$ or $C_6$–$C_{12}$ aryl group (containing 1 or 2 rings) as defined above substituted with a lower alkyl group (as defined above) with the total number of carbon atoms in the arylalkyl group preferably being between 7 and 15, cycloalkyl is preferably a $C_3$–$C_{17}$ cycloalkyl group (containing 1 or 2 cycloalkyl groups), more preferably a $C_3$–$C_{12}$ cycloalkyl group, arylalkoxycarbonyl is preferably an aryl group as defined above substituted with a lower alkoxy group (as defined above) with the total number of carbon atoms in the arylalkoxy group preferably being between 8 and 16 and can include compounds wherein two aryl groups are connected by a cyclic hydrocarbon group, such as Fmoc, and aryloxycarbonyl is preferably an aryl group as defined above having an oxycarbonyl group attached to one of the ring carbon atoms (e.g.

Aryl—O—C(O)—), more preferably a $C_6$–$C_{13}$ aryloxycarbonyl (containing 1 or 2 rings), arylcarbonyl is preferably an aryl group as defined above having a carbonyl group attached to one of the ring carbon atoms (e.g. Aryl—C(O)—), more preferably $C_7$–$C_{16}$ arylcarbonyl (containing 1 or 2 rings), arylacetyl is preferably an aryl group as defined above having an acetyl group attached to one of the ring carbon atoms (e.g. Aryl—CH$_2$—C(O)—), more preferably a $C_8$–$C_{17}$ arylacetyl group (containing 1 or 2 rings) and heterocyclic is preferably a heterocyclic group containing 1 or 2 rings containing at least 1, preferably 1 to 3, more preferably 1 or 2 heteroatoms such as N, O or S wherein the remainder of the ring atoms are carbon atoms, wherein each ring is saturated or unsaturated and contains 4 to 7 ring atoms, with a total of 4 to 11 ring atoms where two fused rings are present.

2. Therapeutic Utility

In the practice of the therapeutic methods of the present invention, an effective amount of the active compound, including derivatives or salts thereof, or a pharmaceutical composition containing the same in combination with a pharmaceutical carrier or diluent, as described below, is administered via any of the usual and acceptable methods known in the art, either singly or in combination with another compound or compounds of the present invention or other pharmaceutical agents such as immunosuppressants, antihistamines, corticosteroids, and the like. These compounds or compositions can thus be administered orally, sublingually, topically (e.g., on the skin or in the eyes), by inhalation, by suppository, or parenterally (e.g., intramuscularly, intravenously, subcutaneously or intradermally), and in the form of either solid or liquid dosage including tablets, suspensions, and aerosols, as is discussed in more detail below. The administration can be conducted in single unit dosage form with continuous therapy or in single dose therapy ad libitum. A unit dose is defined as 1 to 3000 mg for a human patient.

Useful pharmaceutical carriers for the preparation of the pharmaceutical compositions hereof can be solids, liquids or mixtures thereof; thus, the compositions can take the form of tablets, pills, capsules, powders, enterically coated or other protected formulations (such as binding on ion exchange resins or other carriers, or packaging in lipid or lipoprotein vesicles or adding additional terminal amino acids), sustained release formulations, erodible formulations, implantable devices or components thereof, microsphere formulations, solutions (e.g., ophthalmic drops), suspensions, elixirs, aerosols, and the like.

Water, saline, aqueous dextrose, and glycols are preferred liquid carriers, particularly (when isotonic) for injectable solutions. The carrier can be selected from various oils including those of petroleum, animal, vegetable or synthetic origin, for example, peanut oil, soybean oil, mineral oil, sesame oil, and the like. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The compositions may be subjected to conventional pharmaceutical expedients such as sterilization and may contain conventional pharmaceutical additives such as preservatives, stabilizing agents, wetting or emulsifying agents, salts for adjusting osmotic pressure, buffers, and the like. Suitable pharmaceutical carriers and their formulations are described in Martin, "Remington's Pharmaceutical Sciences", 15th Ed.; Mack Publishing Co., Easton (1975); see, e.g., pp. 1405–1412 and pp. 1461–1487. Such compositions will, in general, contain an effective amount of the active compound together with a suitable amount of carrier so as to prepare the proper dosage form for proper administration to the host.

In one preferred embodiment, the therapeutic methods of the present invention are practiced when the relief of symptoms is specifically required or perhaps imminent; in another preferred embodiment, the method hereof is effectively practiced as continuous or prophylactic treatment.

In the practice of the therapeutic methods of the invention, the particular dosage of pharmaceutical composition to be administered to the subject will depend on a variety of considerations including the nature of the disease, the severity thereof, the schedule of administration, the age and physical characteristics of the subject, and so forth. Proper dosages may be established using clinical approaches familiar to the medicinal arts. It is presently believed that dosages in the range of 0.1 to 100 mg of compound per kilogram of subject body weight will be useful, and a range of 1 to 100 mg per kg generally preferred, where administration is by injection or ingestion. Topical dosages may utilize formulations containing generally as low as 0.1 mg of compound per ml of liquid carrier or excipient, with multiple daily applications being appropriate.

The compounds and therapeutic or pharmaceutical compositions of the invention might be useful in the study or treatment of diseases or other conditions which are mediated by the binding of integrin receptors to ligands, including conditions involving inappropriate (e.g., excessive or insufficient) binding of cells to natural or other ligands. Such diseases and conditions might include inflammatory diseases such as rheumatoid arthritis, asthma, allergy conditions, adult respiratory distress syndrome, inflammatory bowel diseases (e.g., ulcerative colitis and regional enteritis) and ophthalmic inflammatory diseases; autoimmune diseases; and cardiovascular disease; prevention of occlusion following thrombolysis; neoplastic disease including metastatic conditions; as well as conditions wherein increased cell binding is desired, as in wound healing or prosthetic implantation situations, as discussed in more detail above.

The compounds of the present invention might find use in the diagnosis of diseases which result from abnormal cell adhesion. For example, excessive adhesion of leukocytes to endothelial cells or to exposed extracellular matrix in blood vessels has been implicated in early stages of atherosclerosis. Thus, a person demonstrating excessive binding of leukocytes to endothelial cells might be at risk for developing occluded arteries. One might detect this risk factor by measuring the binding of a compound of structure I to leukocytes and endothelial cells of the patient thought to be at risk.

Furthermore, the compounds of the present invention might find use in the diagnosis of autoimmune diseases caused by antibodies which bind to cell adhesion molecules or which bind to receptors for cell adhesion molecules. For example, if a disease is caused by antibodies binding to a cell adhesion molecule which is mimicked by a compound of structure I, then a diagnostic test for the presence of such antibodies is easily performed by immunoassay of blood or serum from a patient using a compound of structure I bound to a carrier so as to capture the antibodies. The bound antibody can be detected by the means typical of the art such as a labelled second antibody directed to the Fc portion of human antibodies or using labelled Fc-binding proteins from bacteria (protein A or protein G). In the alternative situation, where the compound of structure I binds to the same receptor as the disease-causing antibody, a competitive immunoassay format can be used. In this format, the compound I is labelled and competition for binding to receptor protein attached to the substrate can be measured.

In addition, derivatives of the present compounds might be useful in the generation of antigens which are prepared by coupling the peptides to a carrier protein. Animals are then immunized with this complex thereby generating antibodies to the peptides. These antibodies will, in some cases, themselves be effective in inhibiting cell adhesion or modulating immune activity by acting as receptors for cell adhesion ligands, or, if anti-idiotypic, by acting to block cellular receptors.

Furthermore, the compounds of the present invention might be used to produce matrices for purifying substances which bind to the compounds of the present invention with high affinity. Such a matrix could be produced, for example, by covalently attaching a compound of the present invention to a derivatized chromatographic support. In one embodiment of this aspect of the invention, a cyclic peptide listed in Table 1 which contains a free amino group can be coupled to a cyanogen bromide activated chromatography resin, such as that available from Pharmacia, (Uppsala, Sweden, Cat. No. 52-1153-00-AK). If necessary, an amino group can be introduced into the desired peptide, either by addition of a lysine residue, or by addition of another amine-containing residue. Alternatively, of course, carbodiimide-activated resin can be used in conjunction with cyclic peptides bearing free carboxyl functions.

The peptide is coupled using the protocol essentially as provided by the manufacturer. The cyclic peptide-derivatized resin can then be used to purify proteins, polysaccharides or the like which may bind the cyclic peptide with high affinity. Such a purification is accomplished by contacting the cyclic peptide-derivatized resin with a sample containing the compound to be affinity purified under conditions which allow formation of the specific complex, washing of the complex bound to the resin with a solution which removes unwanted substances, but leaves the complex intact, and then eluting the substance to be purified by washing the resin with a solution which disrupts the complex.

Compounds of the present invention are expected to be useful in the identification of binding sites of crystalline receptors or ligands. When co-crystallized with the receptor or ligand to be analyzed, these compounds should aid in the identification and structural mapping of relevant binding sites, as well as in the determination of conformational changes which may occur upon binding. Crystallographic analysis will also aid in the selection of compounds of the present invention to be used in pharmaceutical applications.

EXAMPLES

Although any methods and materials similar or equivalent to those described herein can be used in the practice or testing of the present invention, the preferred methods and materials are now described. As set forth above, all publications to which reference is made are incorporated herein by reference.

Example 1

Synthesis and Formation of Compounds

The "backbones," i.e., the peptide-bond linked portions of the cyclic compounds of the invention were generally synthesized using solid phase peptide synthesis as depicted in Table 1, and then cyclized using a procedure in which, where necessary, the appropriate protecting groups were removed prior to cyclization. Other methods for synthesis and cyclization are known in the art and may be employed in the preparation of the cyclic compounds and formulations disclosed herein.

Attachment of N-Boc-S-(4-methylbenzyl)-Cysteine (Boc-Cys-(4-MeBzl) to the chloromethyl polystyrene resin (Merrifield resin) was done in the presence of potassium fluoride (Horiki, *Chem. Lett.*, (#2), 166–168 (1978)).

General Procedures for Synthesis of Cyclic Peptides

Peptide Synthesis: Boc-Cys(4-MeBzl)-polystyrene resin (for C-terminal carboxylic acids) or 4-methylbenzhydrylamine resin (for C-terminal carboxamides) was used for the stepwise assembly of the product peptides using the Boc amino acid procedure in Table 1. Related procedures can be found in the published International Patent Application WO 92/00995, which was previously incorporated by reference. Following coupling of the last amino acid the N-terminal Boc protecting group was removed by mixing the resin with TFA:DCM (1:1) for 20 minutes. Following rinsing in order with DCM (3X), MeOH (2X), DCM (3X) the resin was air dried.

When used in the peptide synthesis, TCA was obtained by the chemical synthesis procedures fully disclosed in the Published International Patent Application WO 94/15958. Those procedures are fully incorporated in their entirety into this application by reference.

Cleavage: The Boc-deprotected peptides on-resin were cleaved by stirring at −5° to 0° C. with a cocktail of distilled anhydrous HF (10 ml/g resin), anisole (1 ml/g resin) and dimethyl sulfide (0.5 ml/g resin). After one hour, the HF was removed under reduced pressure. The cleaved peptide/resin mixture was washed three times with diethyl ether and then extracted with 80% aqueous acetic acid. The combined extracts (100 ml/g or 200 ml/2 g resin) were pooled and carried on to the cyclization step.

Cyclization: The peptides were cyclized through the formation of an amide linkage, a disulfide linkage, a monosulfide linkage or a dithioether linkage, as appropriate.

Purification: The cyclic peptide was purified on a Waters Delta Prep 3000 system (Waters, Milford, Massachusetts) equipped with $C_{18}$ reverse phase column (15–20 mm, 5×30 cm ID), using a linear gradient of increasing acetonitrile concentration in 1.0% triethylammonium phosphate (TEAP, pH 2.3) as the mobile phase. The appropriate fractions were pooled to give the pure peptide as a phosphate salt. The peptide salt was applied again to the column and eluted with a linear gradient of increasing amounts of acetonitrile in 1.0% aqueous HOAc to afford the desired acetate salt form.

Analysis: The purified peptides were analyzed using a Beckman System 126 (Detector module 166), equipped with a Beckman $C_{18}$ column (RPC18 Ultrasphere, 5 μm, 4.6×150 mm ID). Elution was performed with buffer A=0.1M sodium phosphate in water, pH 4.4–4.5, buffer B=60% acetonitrile in buffer A, using a linear gradient of buffer B and a flow rate of 1 ml/minute. The gradient was adjusted for each peptide, to provide elution of the peptide near the middle of the gradient.

TABLE 1

Schedule for Solid Phase Peptide Synthesis
(TFA deprotection/DCC coupling)

| Step | Reagent | Vol* (ml) | Time (min) |
|---|---|---|---|
| 1 | DCM wash (3x) | 20 | 1/wash |
| 2 | TFA-DCM (1:1) | 20 | 1 |
| 3 | TFA-DCM (1:1) | 20 | 20 |
| 4 | DCM wash (3x) | 20 | 1/wash |
| 5 | MeOH wash (2x) | 20 | 1/wash |
| 6 | DCM wash (3x) | 20 | 1/wash |
| 7 | 5% DIEA-DCM (1:9) | 20 | 1 |

TABLE 1-continued

Schedule for Solid Phase Peptide Synthesis
(TFA deprotection/DCC coupling)

| Step | Reagent | Vol* (ml) | Time (min) |
|---|---|---|---|
| 8 | 5% DIEA-DCM (1:9) | 20 | 5 |
| 9 | DCM wash (4x) | 20 | 1/wash |
| 10 | Boc AA (2.0 meq.) in DCM (or DMF)** | 120 | |
| 11 | DCC (2.0 meq.) in DCM | 20 | |
| 12 | Recouple if necessary by repeating steps 4–11 | | |
| 13 | DCM wash (2x) | 20 | 1/wash |
| 14 | 50% CH$_3$OH-DCM wash | 20 | 1/wash |
| 15 | MeOH wash (2x) | 20 | 1/wash |
| 16 | DCM wash (3x) | 20 | 1/wash |
| 17 | 25% (CH3CO)2O-DCM | 20 | 20 |
| 18 | DCM wash (3x) | 20 | 1/wash |
| 19 | MeOH wash (2x) | 20 | 1/wash |
| 20 | DCM wash (3x) | 20 | 1/wash |

*The volume given is for the synthesis using 0.5 meq./gm of growing peptide chain on two grams of resin.
**DMF added where Boc-AA is insoluble in DCM alone.

Procedure A) Synthesis of Amide Linked Side Chain Cyclized Compounds

In this Example, the following compound was synthesized

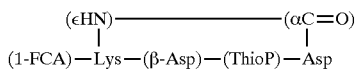

(1-FCA)—Lys—(β-Asp)—(ThioP)—Asp

All natural and synthetic amino acids and derivatives thereof were purchased from BACHEM (Torrance, Calif.). 1-FCA, DCC and diisopropylethylamine and 4-(dimethylamino)-pyridine (DMAP) were obtained from Aldrich (Milwaukee, Wis.). Unless otherwise noted, other reagents were of analytical grade and used without further purification. All residues were linked by the solid phase method using Boc protection.

(1) Synthesis of protected K*(β-D)(ThioP)D* peptide sequence.

Synthesis of the above peptide was performed using, in conjunction, an automated peptide synthesizer (System 990, Beckman Instruments, Inc., Palo Alto, Calif.) and a manual peptide synthesis apparatus (S.C. Glass Tech, Bonica, Calif.). The following amino acids were used in the synthesis: Boc-(ThioP), Boc-β-Asp(α-O-benzyl) and Boc-Lys(N$^\epsilon$-Fmoc). The N-Boc-L-α-Asp-β-fluoromethyl ester was attached to the hydroxymethyl resin using DCC and DMAP as a catalyst (Fehrentz, J. A. and Castro B., *Synthesis*, 676–678 (1983)). Boc-L-α-Asp(OFm)OCH$_2$-resin (1.0 g, 0.75 mmol) was used as the starting resin. Excess amino acid (2–3 fold) was used for each coupling. The peptide chain was constructed on the Beckman peptide synthesizer using Boc chemistry with the stepwise addition of each amino acid following the standardized cycle similar to that presented in Table 1, with adjustments for scale. 50% TFA in DCM, 5% DIEA in DCM, and 0.5M of DCC in DCM were used as deprotecting, neutralizing, and activating agents, respectively, for each cycle.

(2) Synthesis of N-terminal derivatized peptides

Following the removal of the Boc group from the N-terminal Lys with 50% TFA in DCM, the peptide on resin was washed with MeOH (2x1 min) and DCM (3x1 min) and neutralized with 5% DIEA in DCM (2x1 min). The peptide was then washed with DCM (3x1 min) and reacted with 1-FCA and DCC. Any unreacted amino groups were capped with acetic anhydride in DCM.

(3) General cyclization procedure for formation of the amide bridge.

The peptide was cyclized on the resin by forming an amide linkage between the β-carboxyl group of Asp and the ε-amino group of Lys using the following general procedure.

Filtering was performed between each step: (1) MeOH (2x1 min); (2) DCM (3x1 min); (3) 20% piperidine in DMF, wash for 1 min, and deprotection for 20 min; (4) DMF (2x1 min); (5) MeOH (2x1 min); (6) DCM (3x1 min); (7) BOP reagent (4 equiv.) in DMF (20 ml/gram of resin), stir for 2 min. and add DIEA (2% of DMF volume), stir for 4 hrs (the completion of the cyclization reaction was monitored by the ninhydrin test; if the reaction was judged incomplete at 4 hrs, the reaction was continued until the ninhydrin test was negative); wash with (8) DMF (2x1 min); (9) DCM (2x1 min); (10) MeOH (2x1 min).

The final cyclic compound was removed from the resin by treatment with HF in the presence of anisole for 1 hr at 0° C. After removal of the HF, in vacuo, the residue was washed with diethyl ether and the peptide was extracted from the resin with an aqueous HOAc solution. The aqueous extract was lyophilized to yield the crude peptide.

(4) Purification

The compound was purified using a Waters Delta Prep 3000 system (Waters, Milford, Mass.) equipped with a C$_{18}$ column, using a linear gradient of increasing acetonitrile concentration in TEAP (pH 2.2 to 2.4) as the mobile phase. The collected fractions of the pure compound were pooled and applied again to the C$_{18}$ column. This time the sample was eluted with a linear gradient of increasing amounts of acetonitrile in 1.0% aqueous HOAc to convert the phosphate salt form of the peptide to the desired acetate form. The pure peptide fractions were pooled, concentrated in vacuo, redissolved in water and lyophilized to give a white powder.

These synthesis and purification procedures can also be applied to longer cyclic peptide sequences which contain a side chain-side chain cyclizing linkage.

Procedure B) Synthesis of Cyclic Disulfide Compounds

In this example, the following compound was prepared:

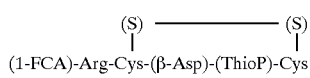

(1-FCA)-Arg-Cys-(β-Asp)-(ThioP)-Cys

All peptides were synthesized by the solid phase method with a Beckman automated peptide synthesizer (System 990, Beckman Instruments, Inc., Palo Alto, Calif.) using Boc chemistry and HF cleavage as discussed above.

Following HF cleavage the peptide was cyclized using a standard iodine cyclization method. (E. Wunsch et al, *Int. J. Peptide Res.*, 32, 368–383 (1988)). After HF cleavage the crude peptide was washed with diethyl ether and then extracted from the resin with 80% aqueous acetic acid in water. The peptide solution was titrated with I$_2$-glacial acetic acid (saturated) until the solution turned light brown in color and stirred for one hour at room temperature. The excess iodine was quenched by adding an ascorbic acid-water solution (saturated). The peptide solution was then concentrated under reduced pressure and purified as described for Procedure A, Section 4.

This procedure can also be used for synthesis and purification of longer cyclic peptide compounds which contain a disulfide linkage.

Procedure C) Synthesis of Cyclic Thioether Compounds

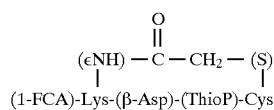
(1-FCA)-Lys-(β-Asp)-(ThioP)-Cys

1-FCA, bromoacetic acid and DCC were purchased from Aldrich Chemical Company (Milwaukee, Wis.). All natural and synthetic amino acids and derivatives thereof were purchased from BACHEM INC. (Torrance, Calif.). Trifluoroacetic acid was from Halocarbon Co. (New York, N.Y.). Triethylamine was from Fisher Scientific (Fall Lawn, N.J.). Other reagents were obtained from conventional sources and of analytical grade.

The peptide was synthesized by the solid phase method with a Beckman automated peptide synthesizer (System 990, Beckman Instruments, Inc., Palo Alto, Calif.). The following amino acids were used in the synthesis: Boc-Lys (Fmoc), Boc-β-Asp(α-O-Bzl) and Boc-(ThioP). Boc-Cys(4-Me-Bzl)—OCH$_2$-polystyrene resin was used for the stepwise assembly of the title peptide, using the Boc amino acid procedure in Table 1. Following capping of the N-terminus with 1-FCA, the Lys N-ε-Fmoc group was removed by treatment with 20% piperidine in DMF. The solution was then stirred for 20 minutes at room temperature and filtered. The resin was washed with DMF. The free Lys side-chain amino group was coupled with bromoacetic acid and after HF cleavage, the peptide was cyclized by forming a monosulfide linkage by the general procedure, as described below.

General Cyclization Procedure for Formation of Monosulfide Linkage

The Lys side-chain deprotected peptide was coupled with bromoacetic acid through the use of DCC in DCM. The mixture was stirred for 2 hours at room temperature (completion of the coupling reaction was monitored by the ninhydrin test). The resin was washed with DCM (3×1 min), MeOH (2×1 min) and DCM (3×1 min).

The bromoacetyl peptide was removed from the resin by treatment with HF in the presence of anisole (1 ml/g resin) and DMS (0.5 ml/g resin) for 1 hr. at 0° C. The HF was removed under reduced pressure. The cleaved mixture was washed three times with diethyl ether and the peptide was extracted into aqueous acetic acid. This bromoacetyl peptide is unstable, and the cyclization to form the monosulfide bridge immediately followed the HF cleavage.

Dilute NH$_4$OH solution was added to the crude peptide extract. The pH was adjusted to 8–9, and the solution was stirred for one hour at room temperature, (completion of the cyclization was monitored by HPLC and the Ellman test). The crude cyclized peptide was purified as described for Procedure A, Section 4.

Procedure D) Synthesis of Cyclic Dithioether

In this example, the following compound was prepared:

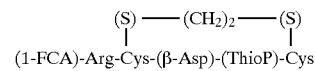
(1-FCA)-Arg-Cys-(β-Asp)-(ThioP)-Cys

1-Fluorenecarboxylic acid, dibromoethane, and DCC were purchased from Aldrich Chemical Company (Milwaukee, Wis.). All amino acids, amino acid derivatives and analogs were purchased from BACHEM INC. (Torrance, Calif.). Trifluoroacetic acid was from Halocarbon Co. (New York, N.Y.). Triethylamine was from Fisher Scientific (Fall Lawn, N.J.). Other reagents were obtained from conventional sources and were of analytical grade.

The peptide was synthesized by the solid phase method with a Beckman automated peptide synthesizer (System 990, Beckman Instruments, Inc., Palo Alto, Cal.). N-Boc-S-9-Fluorenylmethyl-L-Cysteine was attached to the hydroxymethyl resin using DCC and DMAP as a catalyst. The following amino acids were used in the synthesis: Boc-Arg(Tos), Boc-β-Asp(α-O-Bzl) and Boc-(ThioP) . Boc-Cys (Fm)—OCH$_2$-polystyrene resin was used for the stepwise assembly of the peptide following the Boc amino acid procedure in Table 1. Following reaction of the peptide with 1-Fluorenecarboxylic acid at the α-N-terminal Arg, the two Fm-groups were removed from the Cys-side chains by 20% piperidine in DMF, as discussed above. The peptide was cyclized to form the dithioether linkage on the resin by the general procedure below.

General cyclization procedure for formation of dithioether linkage

The dithioether linkage (—S—(CH$_2$)n—S—) was synthesized while the peptide was bound on the resin. After removing the Fm-groups from the Cys-side chains, the dithioether linkage was formed by adding dibromoethane (3 equivalents) and DIEA in DMF. The pH was adjusted to 8–9, and the solution was stirred for 2 to 4 hours at room temperature, (completion of the cyclization was monitored by HPLC and the Ellman test). The peptide was then washed with DMF (2×1 min), DCM (3×1 min), MeOH (2×1 min) and DCM (3×1 min).

The cyclic peptide was removed from the resin by treatment with HF in the presence of anisole for 1 hr. at 0° C. After removal of the HF, in vacuo, the residue was washed with diethyl ether and the peptide was extracted into an aqueous acetic acid solution. The aqueous extract was lyophilized to yield the crude peptide. The crude peptide was purified as described for Procedure A, Section 4.

TABLE 2

Analytical data

| # | Name | Cyclization Procedure | Purity | MS |
|---|------|-----------------------|--------|-----|
| 1) | Arg-Cys*-(β-Asp)-(ThioP)-Cys* | B | 74.5 | |
| 2) | (9-FAc)-Arg-Cys*-(β-Asp)-(ThioP)-Cys* | B | 97.2 | 815 |
| 3) | (Ada)-Arg-Cys*-(β-Asp)-(ThioP)-Cys* | B | 93.6 | 785 |
| 4) | (1-FCA)-Arg-Cys*-(β-Asp)-(ThioP)-Cys* | B | 98.0 | 801 |
| 5) | Trp-Arg-Cys*-(β-Asp)-(ThioP)-Cys* | B | 90.7 | |
| 6) | (5-Finc)-Arg-Cys*-(β-Asp)-(ThioP)-Cys* | B | 97.1 | 770 |

TABLE 2-continued

Analytical data

| # | Name | Cyclization Procedure | Purity | MS |
|---|---|---|---|---|
| 7) | (9-FAc)-Arg-Cys*-(β-Asp)-Asn-Cys* | B | 100 | |
| 8) | (Ac)-Arg-Cys*-(β-Asp)-(ThioP)-Cys*-NH$_2$ | B | 99.2 | 650 |
| 9) | (Ac)-Arg-Cys*-(β-Asp)-(ThioP)-Cys* | B | 99.9 | 651 |
| 10) | (Biotinyl)-Arg-Cys*-(β-Asp)-(ThioP)-Cys* | B | 99.4 | |
| 11) | (1-FCA)-Arg-Cys*-(β-Asp)-(ThioP)-Cys*-NH$_2$ | B | 100 | |
| 12) | (1-FCA)-Gly-Cys*-(β-Asp)-(ThioP)-Cys* | B | 99.5 | |
| 13) | (1-FCA)-Lys-Cys*-(β-Asp)-(ThioP)-Cys* | B | 100 | 773 |
| 14) | (Nα-Me-Arg)-Cys*-(β-Asp)-(ThioP)-Cys* | B | 100 | |
| 15) | (1-FCA)-Arg-Cys*-(β-Asp)-(N-Me-Ala)-Cys* | B | 94.1 | |
| 16) | (S)―――(CH$_2$)$_2$―――(S)<br>\|                    \|<br>(1-FCA)―Arg―Cys*―(β-Asp)―(ThioP)―Cys* | D | 96.7 | |
| 17) | (1-FCA)-(D-Arg)-Cys*-(β-Asp)-(ThioP)-Cys* | B | 99.7 | |
| 18) | (S)―――(CH$_2$)$_3$―――(S)<br>\|                    \|<br>(1-FCA)―Arg―Cys*―(β-Asp)―(ThioP)―Cys* | D | 98.7 | |
| 19) | (9-FCA)-Arg-Cys*-(β-Asp)-(ThioP)-Cys* | B | 100 | |
| 20) | (1-FCA)-Cys*-(β-Asp)-(ThioP)-Cys* | B | 99.4 | |
| 21) | (Fmoc)-Lys(Ada)-Cys*-(β-Asp)-(ThioP)-Cys* | B | 96.4 | |
| 22) | (Fmoc)-Arg-Cys*-(β-Asp)-(ThioP)-Cys* | B | 89.5 | 830 |
| 23) | (For)-Arg-Cys*-(β-Asp)-(ThioP)-Cys* | B | 88.2 | |
| 24) | (For)-Arg-Cys*-(β-Asp)-(ThioP)-Cys*-NH$_2$ | B | 61.4 | |
| 25) | (1-FCA)-Arg-Cys*-(β-Asp)-Ser-(ThioP)-Cys* | B | 99.9 | |
| 26) | (1-FCA)-(Nle)-Cys*-(β-Asp)-(ThioP)-Cys* | B | 100 | |
| 27) | (1-FCA)-Arg-Cys*-(β-Asp)-(ThioP)-Cys*-Ala-Ala | B | 98.6 | |
| 28) | (1-FCA)-Arg-Cys*-(β-Asp)-Ser-(ThioP)-Cys*-Ala-Ala | B | 100 | |
| 29) | Lys(1-NaphAc)-Cys*-(β-Asp)-(ThioP)-Cys* | B | 99.1 | |
| 30) | (1-FCA)-(Cha)-Cys*-(β-Asp)-(ThioP)-Cys* | B | 98.3 | |
| 31) | (Fmoc)-Lys(PhAc)-Cys*-(β-Asp)-(ThioP)-Cys* | B | 82.8 | |
| 32) | (1-FCA)-Lys(For)-Cys*-(β-Asp)-(ThioP)-Cys* | B | 96.2 | |
| 33) | (Fmoc)-Lys(1-NaphAc)-Cys*-(β-Asp)-(ThioP)-Cys* | B | 99.7 | |
| 34) | (Fmoc)-Lys(2-NaphAc)-Cys*-(β-Asp)-(ThioP)-Cys* | B | 99.6 | |
| 35) | (1-FCA)-Arg-Cys*-(β-Asp)-(ThioP)-Cys*-Ala-Ala-Asp-(OFm) | B | 70.8 | |
| 36) | (Ac)-Arg-Cys*-(β-Asp)-(ThioP)-Cys*-Ala-Ala | B | 98.5 | |
| 37) | (Ac)-Arg-Cys*-(β-Asp)-(ThioP)-Cys*-Ala-Asp-(OFm) | B | 99.4 | |
| 38) | (Ac)-Arg-Cys*-(β-Asp)-(ThioP)-Cys*-Ala-Asp-(NH-Ada) | B | 98.4 | |
| 39) | (1-FCA)-Arg-Cys*-(β-Asp)-Gly-(ThioP)-Cys* | B | 99.2 | |
| 40) | (Fmoc)-Lys-Cys*-(β-Asp)-(ThioP)-Cys* | B | 99.1 | 803 |
| 41) | (Ac)-Cys*-(β-Asp)-(ThioP)-Cys*-Lys(Fmoc)-Gly | B | 69.0 | 902 |
| 42) | (1-FCA)-Arg-Cys*-(β-Asp)-(ThioP)-Cys*-Ala-Ala-Ala | B | 90.8 | 773 |
| 43) | (Fmoc)-Orn-Cys*-(β-Asp)-(ThioP)-Cys* | B | 96.2 | |
| 44) | (Fmoc)-Orn(PhAc)-Cys*-(β-Asp)-(ThioP)-Cys* | B | 72.0 | |
| 45) | (1-FCA)-Arg-Cys*-(β-Asp)-(ThioP)-Cys*-Ala-Ser | B | 97.0 | 959 |
| 46) | (9-FAc)-Arg-Cys*-(β-Asp)-(ThioP)-Cys*-Ala-Ala | B | 88.5 | |
| 47) | (2-NaphAc)-Arg-Cys*-(β-Asp)-(ThioP)-Cys*-Ala-Ala | B | 99.5 | |
| 48) | (PhAc)-Arg-Cys*-(β-Asp)-(ThioP)-Cys*-Ala-Ala | B | 98.4 | |
| 49) | (1-NaphSO$_2$)-Arg-Cys*-(β-Asp)-(ThioP)-Cys*-Ala-Ala | B | 99.4 | |
| 50) | (2-NaphSO$_2$)-Arg-Cys*-(β-Asp)-(ThioP)-Cys*-Ala-Ala | B | 83.3 | |
| 51) | (1-FCA)-Arg-Cys*-(β-Asp)-(ThioP)-Cys*-Ala | B | 100 | |
| 52) | (1-FCA)-Arg-Cys*-(β-Asp)-(ThioP)-Cys*-Gly-Gly | B | 76.8 | |
| 53) | (2-NaphCA)-Arg-Cys*-(β-Asp)-(ThioP)-Cys*-Ala-Ala | B | 96.7 | |
| 54) | (9-FAc)-Arg-Cys*-(β-Asp)-(ThioP)-Cys*-Ala-Lys | B | 100 | |
| 55) | (2-NaphAc)-Arg-Cys*-(β-Asp)-(ThioP)-Cys*-Ala-Lys | B | 88.6 | |
| 56) | (2-NaphAc)-Arg-Cys*-(β-Asp)-(ThioP)-Cys*-Ala-Lys(Fmoc)-NH$_2$ | B | 86.9 | |
| 57) | (2-NaphAc)-Arg-Cys*-(β-Asp)-(ThioP)-Cys*-(Abu)-Lys | B | 99.1 | |
| 58) | (9-FCA)-Lys(PhAc)-Cys*-(β-Asp)-(ThioP)-Cys* | B | 89.6 | |
| 59) | (1-FCA)-Lys(PhAc)-Cys*-(β-Asp)-(ThioP)-Cys*-Ala-Ser | B | 96.5 | |
| 60) | (1-FCA)-Lys(PhAc)-Cys*-(β-Asp)-(ThioP)-Cys* | B | | |
| 61) | (9-FCA)-Lys-Cys*-(β-Asp)-(ThioP)-Cys*-Ala-Ala | B | 99.8 | |
| 62) | (1-FCA)-Arg-Cys*-(β-Asp)-(TCA)-Cys* | B | 100 | |
| 63) | (2-NaphAc)-Arg-Cys*-(β-Asp)-(ThioP)-Cys* | B | 100 | |
| 64) | (9-FAc)-Lys-Cys*-(β-Asp)-(ThioP)-Cys* | B | 92.4 | |
| 65) | (9-FAc)-Arg-Cys*-(β-Asp)-(ThioP)-Cys*-(Abu)-Lys | B | 98.4 | |
| 66) | (9-FCA)-Lys(PhAc)-Cys*-(β-Asp)-(ThioP)-Cys*-Ala-Ala | B | 99.3 | |
| 67) | (1-FCA)-Lys*-(β-Asp)-(ThioP)-Asp* | A | 95.5 | |

TABLE 2-continued

Analytical data

| # | Name | Cyclization Procedure | Purity | MS |
|---|------|----------------------|--------|-----|
| 68) | (1-FCA)—Lys*—(β-Asp)—(ThioP)—Cys*  with (HN)—C(=O)—CH$_2$—(S) bridge from Lys to Cys | C | 100 | |
| 69) | (9-FAc)-Lys(PhAc)-Cys*-(β-Asp)-(ThioP)-Cys*-Ala-Ser | B | 88.2 | |
| 70) | (Xan)-Arg-Cys*-(β-Asp)-(ThioP)-Cys* | B | 94.8 | |
| 71) | (PhAc)-Arg-Cys*-(β-Asp)-(ThioP)-Cys* | B | 100 | |
| 72) | (Fmoc)-Arg-Cys*-(β-Asp)-Pro-Cys* | B | 99.0 | 813 |
| 73) | (Fmoc)-Arg-Cys*-(β-Asp)-(Aib)-Cys* | B | 99.9 | 801 |
| 74) | (Fmoc)-Arg-Cys*-(β-Asp)-Ala-Cys* | B | 91.9 | 787 |
| 75) | (Fmoc)-Arg-Cys*-(β-Asp)-(N-Me-Ala)-Cys* | B | 99.0 | 801 |
| 76) | (Fmoc)-Arg-Cys*-(β-Asp)-(Tic)-Cys* | B | 99.9 | 875 |
| 77) | (Fmoc)-Arg-Cys*-(β-Asp)-Pro-Cys*-NH$_2$ | B | 99.9 | 812 |
| 78) | (Fmoc)-Arg-Cys*-(β-Asp)-(N-Me-Ala)-Cys*-NH$_2$ | B | 98.0 | 800 |
| 79) | (Fmoc)-Arg-Cys*-(D-β-Asp)-(ThioP)-Cys* | B | 96.0 | 831 |
| 80) | (Fmoc)-Arg-Cys*-(β-Asp)-(ThioP)-(D-Cys*) | B | 99.0 | 831 |
| 81) | (Fmoc)-Arg-Cys*-(β-Asp)-(D-Pro)-Cys* | B | 99.9 | 813 |
| 82) | (Fmoc)-Arg-(Pen)*-(β-Asp)-(ThioP)-Cys* | B | 98.0 | 859 |
| 83) | (Fmoc)-Arg-Cys*-(β-Asp)-(ThioP)-(Pen)* | B | 99.0 | 858 |
| 84) | (Fmoc)-Arg-(D-Pen)-*-(β-Asp)-(ThioP)-(D-Pen)* | B | 99.0 | 887 |
| 85) | (Fmoc)-Arg-Cys*-(β-Asp)-Cys* | B | 96.0 | 716 |
| 86) | (Ac)-Cys*-((β-Asp)(OFin))-(ThioP)-Cys* | B | 99.0 | 673 |

*denotes residue utilized in the cyclization of the compound
Amino acids of the peptide backbone are delineated with hyphens; synthetic amino acids, unnatural amino acids, and amino acid mimetics are enclosed in parentheses; the $R^1$–$R^5$ groups which are attached to the backbone amino acid groups are enclosed in parentheses and are immediately adjacent to the amino acid to which it is attached without an intervening hyphen.
In Table 2, the amino acid without an indication of enantiomeric structure means L-enantiomer.

Example 2

Cell Adhesion Inhibition Assays
Jurkat-Endothelial Cell Adhesion Assay

The following assay established the activity of the present compounds in inhibiting $\beta_1$-mediated cell adhesion in a representative in vitro system. This assay measured the adhesive interactions of a T-cell line, Jurkat, known to express high levels of $\alpha_4\beta_1$, to endothelial cell monolayers in the presence of representative test compounds of the present invention. The test compounds were added in increasing concentrations to T-cells and then the T-cell/compound mixture was added to IL-1 stimulated endothelial cell monolayers. The plates were incubated, washed and the percentage of attached cells was quantitated. The present assay directly demonstrated the cell adhesion inhibitory activity and adhesion modulatory activity of the present compounds.

Human umbilical vein endothelial cells (HUVEC) were purchased from Clonetics (San Diego, Calif.) at passage number 2. The cells were grown on 0.5% porcine skin gelatin pre-coated flasks (Sigma, St. Louis, Mo.) in EGM-UV media (Clonetics, San Diego, Calif.) supplemented with 10% fetal bovine serum. Cells were re-fed every 2–3 days, reaching confluence by day 4 to 6. The cells were monitored for factor VIII antigen and our results showed that at passage 12, the cells are positive for this antigen. The endothelial cells were not used following passage 7.

The T-cell line Jurkat was obtained from American Type Culture Collection and cultured in RPMI media containing 10% fetal calf serum. The cells were washed twice in Hank's buffered saline solution (HBSS) and resuspended in Dulbecco's Minimal Eagle's Media (DMEM) containing 2.5 mg/ml Human Serum Albumin (HSA). Jurkat cells ($1 \times 10^6$ cells/ml) were stained with 10 ng/ml BCECF-AM (Molecular Probes, Eugene, Oreg.) in HBSS without phenol red. The cells were loaded with the BCECF-AM for 60 minutes in the dark at 37° C., washed 2 times, and resuspended in DMEM-HSA solution.

Confluent endothelial monolayers, grown in 96-well tissue culture plates, were stimulated for 4 hours at 37° C. with 0.1 ng/ml (50 U/ml) recombinant IL-1 (Amgen, Thousand Oaks, Calif.). Following this incubation, the monolayers were washed twice with HBSS and 0.1 ml of DMEM-HSA solution was added. Jurkat cells ($5 \times 10^5$ cells) were combined with the appropriate concentration of peptide and 0.1 ml of the Jurkat cell-peptide mixture was added to the endothelial cell monolayers. Generally, 250, 50, 10 and 2 $\mu$M peptide concentrations were tested. With several potent peptides the IC$_{50}$ was determined by testing the peptides at 50, 10, 2 and 0.4 $\mu$M. The plates were placed on ice for 5 minutes to allow for Jurkat cell settling and the plates were incubated at 37° C. for 20 minutes. Following this incubation, the monolayers were washed twice with PBS containing 1 mM calcium chloride and 1 mM magnesium chloride and the plates were read using a Millipore Cytofluor 2300 (Marlboro, Mass.). Fluorescence in each well was measured as Arbitrary Fluorescence Units and percent adhesion in the absence of peptide was adjusted to 100% and the % adhesion in the presence of peptides was calculated. Monolayers were also fixed in 3% paraformaldehyde and evaluated microscopically to verify the adhesion.

The JY-Endothelial Cell Assay

The following assay established the activity of the present compounds in inhibiting cell adhesion through $\beta_2$ integrins in a representative in vitro system. The present assay directly demonstrated the anti-$\beta_2$ adhesion activity and adhesion modulatory activity of the present compounds.

The human B cell line, JY, was cultured in RPMI media containing 10% fetal calf serum at 37° C., in a humidified $CO_2$ atmosphere. Endothelial cells were grown to confluency in 96-well micro-titer assay plates, as in the Jurkat-EC assay. Before the assay, the endothelial cells were stimulated with 50 U/ml rTNF for 18–24 hours at 37° C. JY cells were loaded with the fluorescent dye indicator BCECF-AM as follows: JY cells were washed twice with HBSS and cells were resuspended in HBSS at $5 \times 10^6$ cells/ml; BCECF-AM (Molecular Probes), stock concentration=1 mg/ml in DMSO, was added to the JY cells to a final concentration of 2 μg/ml; cells were incubated in the dark at 37° C. for 30–45 minutes; washed twice with HBSS and used in the assay.

The compounds presented in this invention were typically dissolved in 2.5 mg HSA/ml DME at four times the assay concentration and Ph adjusted with 7.5% Na bicarbonate, as needed.

TNF-stimulated HUVEC were washed twice with HBSS (at room temp). 50 μl of cold HSA-DME was added to each well and the plate transferred to ice. While on ice, the following components were added to the wells in the indicated order:

1) 50 μl test compound
2) 50 μl BCECF-labelled JY cells
3) 50 μl PMA (50 ng/ml)

The assay plates were then typically incubated for 30 min at 37° C. and washed four times with PBS containing $Mg^{2+}$ and $Ca^{2+}$ (room temp). 100 μl of PBS containing $Mg^{2+}$ and $Ca^{2+}$ were added to each well and the fluorescence from the adherent BCECF-labelled cells was analyzed using a fluorescence plate reader. Controls were included which were −TNF/+PMA, +TNF/−PMA, +TNF/+PMA (without compound) and either anti-LFAα or anti-LFAβ supernatants.

Results of Jurkat-Endothelial Cell Adhesion

The above-described adhesion assay yielded the following results for the inhibition of Jurkat cell adhesion to IL-1 stimulated endothelial cells.

Results of JY-Endothelial Cell Adhesion

The above-described adhesion assay yielded the following results for the inhibition of JY cell adhesion to TNF stimulated endothelial cells.

Thus an objective of the present invention is to provide compounds having extraordinarily high potencies in modulating cell adhesion to VCAM and ICAM through $\beta_1$ and $\beta_2$ integrins, respectively, including but not limited to inhibition of T-cell adhesion to endothelial cells. The exact receptors involved in this interaction and the specific receptors targeted by the test compounds include, but are not limited to, $\alpha_4\beta_1$, $\alpha_4\beta_7$, $\alpha_V\beta_1$, $\alpha_L\beta_2$, and $\alpha_M\beta_2$.

The following table 3 shows results from three of the above assays using data from various compounds of the present invention.

TABLE 3

| | compounds: | $IC_{50}$[1] for adhesion inhibition[2] | |
|---|---|---|---|
| # | Name | JY-EC | Jurk-EC |
| 2) | (9-FAc)-Arg-Cys*-(β-Asp)-(ThioP)-Cys* | 141 | 3 |
| 4) | (1-FCA)-Arg-Cys*-(β-Asp)-(ThioP)-Cys* | 61 | 0.3 |
| 8) | (Ac)-Arg-Cys*-(β-Asp)-(ThioP)-Cys*-NH₂ | 169 | 84 |
| 11) | (1-FCA)-Arg-Cys*-(β-Asp)-(ThioP)-Cys*-NH₂ | 175 | |
| 13) | (1-FCA)-Lys-Cys*-(β-Asp)-(ThioP)-Cys* | 68 | <2 |
| 19) | (9-FCA)-Arg-Cys*-(β-Asp)-(ThioP)-Cys* | 54 | |
| 22) | (Fmoc)-Arg-Cys*-(β-Asp)-(ThioP)-Cys*-NH₂ | 52 | |
| 24) | (For)-Arg-Cys*-(β-Asp)-(ThioP)-Cys*-NH₂ | 393 | |
| 26) | (1-FCA)-(Nle)-Cys*-(β-Asp)-(ThioP)-Cys* | 218 | |
| 27) | (1-FCA)-Arg-Cys*-(β-Asp)-(ThioP)-Cys*-Ala-Ala | 51 | |
| 31) | (Fmoc)-Lys(PhAc)-Cys*-(β-Asp)-(ThioP)-Cys* | | 87 |
| 33) | (Fmoc)-Lys(1-NaphAc)-Cys*-(β-Asp)-(ThioP)-Cys* | | 88 |
| 34) | (Fmoc)-Lys(2-NaphAc)-Cys*-(β-Asp)-(ThioP)-Cys* | | 148 |
| 35) | (1-FCA)-Arg-Cys*-(β-Asp)-(ThioP)-Cys*-Ala-Ala-Asp-(OFm) | | 267 |
| 37) | (Ac)-Arg-Cys*-(β-Asp)-(ThioP)-Cys*-Ala-Asp-(OFm) | | 106 |
| 40) | (Fmoc)-Lys-Cys*-(β-Asp)-(ThioP)-Cys* | | 436 |
| 41) | (Ac)-Cys*-(β-Asp)-(ThioP)-Cys*-Lys-(Fmoc)-Gly | | 78 |
| 43) | (Fmoc)-Orn-Cys*-(β-Asp)-(ThioP)-Cys* | | 165 |
| 44) | (Fmoc)-Orn-(PhAc)-Cys*-(β-Asp)-(ThioP)-Cys* | | 81 |
| 45) | (1-FCA)-Arg-Cys*-(β-Asp)-(ThioP)-Cys*-Ala-Ser | | 63 |
| 46) | (9-FAc)-Arg-Cys*-(β-Asp)-(ThioP)-Cys*-Ala-Ala | | 56 |
| 47) | (2-NaphAc)-Arg-Cys*-(β-Asp)-(ThioP)-Cys*-Ala-Ala | | 79 |
| 49) | (1-NaphSO₂)-Arg-Cys*-(β-Asp)-(ThioP)-Cys*-Ala-Ala | | 239 |
| 50) | (2-NaphSO₂)-Arg-Cys*-(β-Asp)-(ThioP)-Cys*-Ala-Ala | | 194 |
| 51) | (1-FCA)-Arg-Cys*-(β-Asp)-(ThioP)-Cys*-Ala | | 101 |
| 52) | (1-FCA)-Arg-Cys*-(β-Asp)-(ThioP)-Cys*-Gly-Gly | | 64 |
| 53) | (2-NaphCA)-Arg-Cys*-(β-Asp)-(ThioP)-Cys*-Ala-Ala | | 387 |
| 54) | (9-FAc)-Arg-Cys*-(β-Asp)-(ThioP)-Cys*-Ala-Lys | | 197 |
| 55) | (2-NaphAc)-Arg-Cys*-(β-Asp)-(ThioP)-Cys*-Ala-Lys | | 251 |
| 56) | (2-NaphAc)-Arg-Cys*-(β-Asp)-(ThioP)-Cys*-Ala-Lys(Fmoc)-NH₂ | | 245 |
| 58) | (9-FCA)-Lys(PhAc)-Cys*-(β-Asp)-(ThioP)-Cys* | | 70 |
| 59) | (1-FCA)-Lys(PhAc)-Cys*-(β-Asp)-(ThioP)-Cys*-Ala-Ser | | 63 |
| 60) | (1-FCA)-Lys(PhAc)-Cys*-(β-Asp)-(ThioP)-Cys* | | 71 |
| 61) | (9-FCA)-Lys-Cys*-(β-Asp)-(ThioP)-Cys*-Ala-Ala | 117 | |
| 64) | (9-FAc)-Lys-Cys*-(β-Asp)-(ThioP)-Cys* | 133 | |
| 65) | (9-FAc)-Lys-Cys*-(β-Asp)-(ThioP)-Cys*-(Abu)-Lys | 353 | |

TABLE 3-continued

| | compounds: | IC$_{50}$[1] for adhesion inhibition[2] | |
|---|---|---|---|
| # | Name | JY-EC | Jurk-EC |
| 68) | 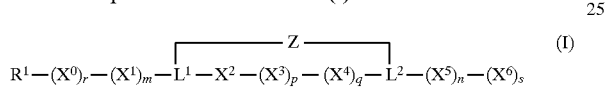<br>(1-FCA)—Lys*—(β-Asp)—(ThioP)—Cys* | 190 | |
| 69) | (9-FAc)-Lys(PhAc)-Cys*-(β-Asp)-(ThioP)-Cys*-Ala-Ser | 94 | |
| 70) | (Xan)-Arg-Cys*-(β-Asp)-(ThioP)-Cys* | 92 | 10 |
| 72) | (Fmoc)-Arg-Cys*-(β-Asp)-Pro-Cys* | 60 | |
| 74) | (Fmoc)-Arg-Cys*-(β-Asp)-Ala-Cys* | 343 | |
| 76) | (Fmoc)-Arg-Cys*-(β-Asp)-(Tic)-Cys* | 457 | |
| 77) | (Fmoc)-Arg-Cys*-(β-Asp)-Pro-Cys*-NH$_2$ | 163 | |
| 85) | (Fmoc)-Arg-Cys*-(β-Asp)-Cys* | 126 | |
| 86) | (Ac)-Cys*-(β-Asp(OFm))-(ThioP)-Cys* | 86 | |

[1]IC$_{50}$ for adhesion inhibition
[2]For detailed description of the tests used see patent body
*denotes residue utilized in the cyclization of the compound
In Table 3, the amino acid without an indication of enantiomeric structure means L-enantiomer.

We claim:

1. A compound of the formula (I):

$$R^1-(X^0)_r-(X^1)_m-\overset{\lceil\phantom{xxx}Z\phantom{xxx}\rceil}{L^1-X^2-(X^3)_p-(X^4)_q-L^2}-(X^5)_n-(X^6)_s \quad (I)$$

or a pharmaceutically acceptable salt thereof, wherein
$L^1$ is selected from the group consisting of a residue of an amino acid and an amino acid mimetic, having a functional group suitable for the formation of a cyclizing moiety or bond, Z, between $L^1$ and $L^2$;
$L^2$ is selected from the group consisting of a residue of an amino acid and an amino acid mimetic, having a functional group suitable for the formation of a cyclizing moiety or bond, Z, between $L^1$ and $L^2$;
Z is a cyclizing moiety or bond between $L^1$ and $L^2$;
$X^0$ is selected from the group consisting of a residue of an amino acid and an amino acid mimetic;
r is an integer of 0 or 1;
$X^1$ is selected from the group consisting of a residue of an amino acid and an amino acid mimetic;
m is an integer of 0, 1 or 2;
$X^2$ is selected from the group consisting of β-Asp, β-Asp ($R^3$), γ-Glu and γ-Glu($R^3$), wherein $R^3$ is selected from the group consisting of —OR, —NHR and —NRR, wherein R is selected from the group consisting of a hydrogen atom, a lower alkyl, an aryl, an arylalkyl, a cycloalkyl, a heteroaryl-lower alkyl and a heterocyclic group;
$X^3$ is selected from the group consisting of Ser($R^4$), Thr($R^4$), Tyr($R^4$), Ala, Gly, Lys($R^4$), Orn($R^4$), Dpr($R^4$), N-Me-Ala, Aib, Val, Tic, o-halo-Tyr, m-halo-Tyr, dihalo-Tyr, p-halo-Phe, dihalo-Phe, Sar, Leu, Ile, Nle and Cys($R^4$), wherein when $X^3$ is Ser($R^4$), Thr($R^4$) or Tyr($R^4$), then $R^4$ is a substituent of the side chain hydroxyl group of $X^3$ and is selected from the group consisting of a hydrogen atom, a lower alkyl, a cycloalkyl, a cycloalkyl-lower alkanoyl, an aryl, an arylalkyl, an aryloxycarbonyl, an arylcarbonyl, a heteroaryl-lower alkyl, an arylacetyl, a heterocyclic group, a lower alkanoyl or an arylalkoxycarbonyl, when $X^3$ is Lys($R^4$), Orn($R^4$) or Dpr($R^4$), then $R^4$ is a substituent of the side chain terminal amino group of $X^3$ and is selected from the group consisting of a hydrogen atom, lower alkyl, a cycloalkyl, a lower alkanoyl, an arylalkyl, an arylalkoxycarbonyl, an aryl, an aryloxycarbonyl, an arylcarbonyl, an arylacetyl, a cycloalkyl-lower alkanoyl, when $X^3$ is Cys($R^4$), then $R^4$ is a substituent of the side chain sulfhydryl group of $X^3$ and is selected from the group consisting of a hydrogen atom, lower alkyl, an arylalkyl, an aryl, a cycloalkyl, an aryloxycarbonyl, an arylcarbonyl, an acetamido-lower alkyl, an arylacetyl or a heterocyclic group, lower alkanoyl, an arylalkoxycarbonyl, a cycloalkyl-lower alkanoyl;
p is an integer of 0 or 1;
$X^4$ is selected from the group consisting of Pro, ThioP, Aib, TTC, Asn, TCA, Sar, an N-methylated natural amino acid, Tic and pipecolinic acid;
q is an integer of 0 or 1;
$X^5$ is a residue of an amino acid or an amino acid mimetic;
n is an integer of 0, 1, 2 or 3;
$X^6$ is selected from the group consisting of a residue of an amino acid and an amino acid mimetic;
s is an integer of 0 or 1; and
$R^1$ is selected from the group consisting of a hydrogen atom, Xan, Fmoc, 9-FAc, 9-FCA, 1-FCA, Ac, 2-NaphAc, Ada, 5-Finc, biotinyl, Su, 1-NaphCA, For, 1-NaphAc, PhAc, 1-NaphSO$_2$, 2-NaphSO$_2$ and 2-NphCA,
with the proviso that the compound (Fmoc)-Arg-Cys*-(β-Asp)-(ThioP)-Cys* is excluded.

2. A compound of claim 1, wherein $X^0$ is Trp and $X^1$ is side chain-protected basic amino acid residue having a side chain terminal amino group with the formula —NHR$^2$, where R$^2$ is selected from the group consisting of a hydrogen atom, PhAc, 1-NaphAc, 2-NaphAc, Ada, 2-norbornylacetyl, 1-FCA, CHAc and For.

3. A compound of claim 1, wherein the α-carboxyl group of $X^2$ has the formula —C(O)R$^3$, where R$^3$ is selected from the group consisting of —OR, —NHR and —NRR; and R is selected from the group consisting of a hydrogen atom, a lower alkyl, an aryl, a cycloalkyl, a heteroaryl-lower alkyl, a heterocyclic group and an arylalkyl.

4. A compound of claim 3, wherein R is selected from the group consisting of Fm, methyl, benzyl, cyclohexyl, isobutyl, 1-naphthylmethyl, 2-naphthylmethyl, 1-adamantyl, 2-picolyl, 3-picolyl and, 4-picolyl.

5. A compound of claim 1, wherein $X^3$ is selected from the group consisting of Ser($R^4$), Thr($R^4$) and Tyr($R^4$); $R^4$ is a substituent of the side chain hydroxyl group of $X^3$ and is selected from the group consisting of a hydrogen atom, a lower alkyl, a cycloalkyl, an aryl, a cycloalkyl-lower alkanoyl, an aryloxycarbonyl, an arylcarbonyl, a heteroaryl-lower alkyl, an arylacetyl, a heterocyclic group, a lower alkanoyl, an arylalkoxycarbonyl and an arylalkyl.

6. A compound of claim 5, wherein $R^4$ is selected from the group consisting of methyl, benzyl, cyclohexyl, 1-naphthylmethyl, 2-naphthylmethyl, Fm, 2-picolyl, 3-picolyl, 4-picolyl and isobutyl.

7. A compound of claim 1, wherein $X^3$ is selected from the group consisting of Lys($R^4$), Orn($R^4$) and Dpr($R^4$), where $R^4$ is a substituent of the side chain terminal amino group of $X^3$ and is selected from the group consisting of a hydrogen atom, a lower alkyl, an aryl, a cycloalkyl, a lower alkanoyl, an arylalkyl, an arylalkoxycarbonyl, an aryloxycarbonyl, an arylcarbonyl, an arylacetyl and a cycloalkyl-lower alkanoyl.

8. A compound of claim 7, wherein $R^4$ is selected from the group consisting of cyclohexyl, 1-naphthylmethyl, 2-naphthylmethyl, Fmoc, 1-FCA, 9-FCA, Ada, Ac and 9-FAc.

9. A compound of claim 1, wherein $X^5$ and/or $X^6$ is a side chain-protected derivative of a basic amino acid residue having a side chain terminal amino group with the formula —$NHR^4$, where $R^4$ is selected from the group consisting of a hydrogen atom, a lower alkyl, an aryl, a cycloalkyl, a cycloalkyl-lower alkanoyl, an arylalkyl, an arylalkoxycarbonyl, a lower alkanoyl, a heterocyclic group, an aryloxycarbonyl, an arylcarbonyl and an arylacetyl.

10. A compound of claim 9, wherein $R^4$ is selected from the group consisting of Ada, cyclohexyl, 1-naphthylmethyl, 2-naphthylmethyl, Ac, Fmoc, 9-FAc, 9-FCA and 1-FCA.

11. A compound of claim 1, wherein $X^5$ and/or $X^6$ is a side chain-protected derivative of an acidic amino acid residue having a side chain terminal carboxyl group with the formula —C(O)$R^4$, where $R^4$ is selected from the group consisting of —OR, —NHR and —NRR; and R is selected from the group consisting of a hydrogen atom, a lower alkyl, a cycloalkyl, a heteroaryl-lower alkyl, a heterocyclic group, an aryl and an arylalkyl.

12. A compound of claim 11, wherein R is selected from the group consisting of Fm, methyl, isobutyl, benzyl, cyclohexyl, 1-naphthylmethyl, 2-naphthylmethyl, 2-picolyl, 3-picolyl, 4-picolyl and 1-adamantyl.

13. A compound of claim 1, wherein $X^5$ and/or $X^6$ is selected from the group consisting of Ser($R^4$), Thr($R^4$), Tyr($R^4$) and side-chain hydroxyl containing synthetic amino acids; $R^4$ is a substituent of the side hydroxyl groups of $X^5$ and/or $X^6$ and $R^4$ is selected from the group consisting of a hydrogen atom, a lower alkyl, a cycloalkyl, a heteroaryl-lower alkyl, an aryloxycarbonyl, an arylcarbonyl, an arylacetyl, a heterocyclic group, an aryl, an arylalkyl, a cycloalkyl-lower alkanoyl, a lower alkanoyl and an arylalkoxycarbonyl.

14. A compound of claim 13, wherein $R^4$ is selected from the group consisting of Fm, methyl, isobutyl, benzyl, cyclohexyl, 1-naphthylmethyl, 2-naphthylmethyl, 2-picolyl, 3-picolyl and 4-picolyl.

15. A compound of claim 1, wherein $X^3$ and/or $X^5$ and/or $X^6$ is selected from the group consisting of Cys($R^4$) and sulfhydryl side-chain containing synthetic amino acids; $R^4$ is a substituent of the side chain sulfhydryl group of $X^5$ and/or $X^6$ and $R^4$ is selected from the group consisting of a hydrogen atom, a lower alkyl, an aryl, a cycloalkyl, an acetamido-lower alkyl, an aryloxycarbonyl, an arylcarbonyl, an arylacetyl, a cycloalkyl-lower alkanoyl, a heterocyclic group, an arylalkyl, a lower alkanoyl and an arylalkoxycarbonyl.

16. A compound of claim 15, wherein $R^4$ is selected from the group consisting of methyl, benzyl, Fm, cyclohexyl, 1-naphthylmethyl, 2-naphthylmethyl, Acm, 4-methylbenzyl and Ada.

17. A compound of claim 1, wherein the C-terminal α-carboxyl group has the formula —C(O)$R^5$, where $R^5$ is selected from the group consisting of —OR, —NHR and —NRR and R is selected from the group consisting of a hydrogen atom, a lower alkyl, an aryl, a cycloalkyl, a heteroaryl-lower alkyl, a heterocyclic group and an arylalkyl.

18. A compound of claim 17, wherein R is selected from the group consisting of Fm, benzyl, cyclohexyl, 1-naphthylmethyl, 2-naphthylmethyl, methyl, isobutyl, 2-picolyl, 3-picolyl, 4-picolyl and 1-adamantyl.

19. A compound of claim 1, wherein $L^1$ is selected from the group consisting of Cys, Arg, Pen, Orn, Lys, Dpr, Gly, Met, Glu and Asp, provided that when $X^0$ or $X^1$ is present, $L^1$ is not Arg or Gly;

$L^2$ is selected from the group consisting of Cys, Cys—$NH_2$, Pen, Orn, Lys, Dpr, Met, Glu and Asp, provided that when $X^5$ or $X^6$ is present, $L^2$ is not Cys—$NH_2$;

Z is selected from a single bond, a lower alkylene or a group of the formula: —$COCH_2$—;

$X^0$ is selected from the group consisting of Trp, 1-Nal, 2-Nal, Tyr, Leu, Nle, Ile, Val, NorVal and Cha;

$X^1$ is selected from the group consisting of Lys($R^2$), Gly, Nα-Me-Arg, Nle, Cha, Val, NorVal, Dpr($R^2$), Arg, Orn($R^2$), Leu, Ile and Abu;

$R^2$ is selected from a hydrogen atom, Ada, 2-norbornylacetyl, 1-FCA, 1-NaphAc, 2-NaphAc, PhAc, For or CHAc;

$X^2$ is selected from the group consisting of β-Asp and β-Asp($R^3$), γ-Glu and γ-Glu($R^3$) and $R^3$ is —OR, —NHR or —NRR and where R is a hydrogen atom, a lower alkyl, an aryl, an arylalkyl, cycloalkyl, a heteroaryl-lower alkyl or heterocyclic group; and $X^5$ and/or $X^6$ is selected from the group consisting of Ala; Asp($R^4$) and Glu($R^4$) wherein $R^4$ is a substituent of the derivatized side chain terminal carboxyl group and is selected from the group consisting of —OR, —NRR and —NHR where R is selected from the group consisting of a hydrogen atom, a lower alkyl, an aryl, a cycloalkyl, a heteroaryl-lower alkyl, a heterocyclic group and an arylalkyl; Ser($R^4$), Tyr($R^4$) and Thr($R^4$) wherein $R^4$ is a substituent of the derivatized side chain hydroxyl group and is selected from the group consisting of H, a lower alkyl, a cycloalkyl, an aryl and an arylalkyl; Gly; Abu; Lys($R^4$); Dpr($R^4$) and Orn($R^4$) wherein $R^4$ is a substituent of the derivatized side chain terminal amino group and is selected from the group consisting of H, a lower alkyl, a cycloalkyl, a lower alkanoyl, an aryl alkyl, an arylalkoxycarbonyl, an aryl, an aryloxycarbonyl, an arylcarbonyl and an arylacetyl; AnC; Leu; Val; Ile; Nle; β-Ala and Cys($R^4$) wherein $R^4$ is a substituent of the derivatized side chain sulfhydryl group and is selected from the group consisting of a lower alkyl, a cycloalkyl, an acetamido-lower alkyl, an aryl and an arylalkyl.

20. A compound of claim 19, wherein $R^1$ is selected from the group consisting of hydrogen, Xan, 9-FAc, 9-FCA, 1-FCA, Ac, 2-NaphAc, Ada, 5-Finc, biotinyl, Su, 1-NaphCA, For, 1-NaphAc, PhAc, 1-NaphSO$_2$, 2-NaphSO$_2$ and 2-NaphCA.

21. A compound of claim 19, wherein p is an integer of 1.

22. A compound of claim 1, wherein Z is selected from a single bond, a lower alkylene or a group of the formula: —COCH$_2$—;

R$^1$ is selected from hydrogen, 1-FCA, 9-FAc, Ada, 5-Finc, Ac, Biotinyl, 9-FCA, Fmoc, For, 9-FAc, 2-NaphAc, PhAc, 1-NaphSO$_2$, 2-NaphSO$_2$, 2-NaphCA or Xan;

X$^0$ is Trp;

r is an integer of 0 or 1;

X$^1$ is selected from Arg, Nu-Me-Arg, Lys, Lys(Ada), Lys(1-NaphAc), Lys(PhAc), Lys(For), Lys(2-NaphAc), Orn, Orn(PhAc), Gly, Nle or Cha;

m is an integer of 0 or 1;

L$^1$ is selected from Cys, Lys or Pen;

X$^2$ is selected from β-Asp or β-Asp(αOFm);

X$^3$ is selected from Ser, N-Me-Ala, Gly or Ala;

X$^4$ is selected from ThioP, Asn, TCA, Pro, Aib or Tic;

L$^2$ is selected from Cys, Cys—NH$_2$, Asp or Pen;

X$^5$ is selected from Ala, Gly, Abu or Lys(Fmoc); and

X$^6$ is selected from Asp-(OFm), Asp-(NH-Ada), Ser, Lys, Lys(Fmoc)—NH$_2$ or Gly.

23. A compound of claim 22, wherein R$^1$ is selected from hydrogen, 1-FCA, 9-FAc, Ada, 5-Finc, Ac, Biotinyl, 9-FCA, For, 9-FAc, 2-NaphAc, PhAc, 1-NaphSO$_2$, 2-NaphSO$_2$, 2-NaphCA or Xan.

24. A compound of claim 23, wherein:

Z is a single bond;

R$^1$ is selected from 1-FCA, 9-FAc, Ac or Xan;

r is an integer of 0;

X$^1$ is selected from Arg or Lys;

m is an integer of 1;

L$^1$ is Cys;

X$^2$ is β-Asp;

p is an integer of 0;

X$^4$ is ThioP;

q is an integer of 1;

L$^2$ is selected from Cys or Cys—NH$_2$;

n is an integer of 0; and s is an integer of 0.

25. A compound of the formula:

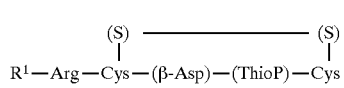

wherein R$^1$ is a substituent of the α-amino group of Arg and is selected from the group consisting of 9-FCA, 1-FCA, 9-FAc, Xan, For, Ac, H, Ada, 5-Finc, PhAc, Su and biotinyl.

26. A compound of the formula:

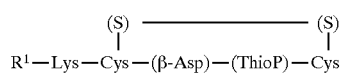

wherein R$^1$ is a substituent of the α-amino group of Lys and is selected from the group consisting of 9-FCA, Fmoc, 1-FCA and 9-FAc.

27. A compound of the formula:

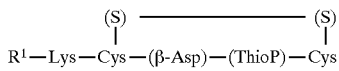

wherein R$^1$ is a substituent of the α-amino group of Lys and is selected from the group consisting of Fmoc, 9-FCA, and 1-FCA; and the ε-amino terminal group of Lys is denoted as NHR$^2$ where R$^2$ is selected from the group consisting of 1-NaphAc, 2-NaphAc, H, For and PhAc.

28. A compound of the formula:

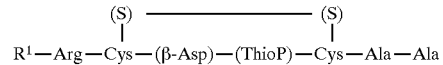

wherein R$^1$ is a substituent of the α-amino group of Arg and is selected from the group consisting of 2-NaphAc, 9-FCA, 1-FCA, 2-NaphCA, Ac, PhAc, 1-NaphSO$_2$ and 2-NaphSO$_2$.

29. A compound of the formula:

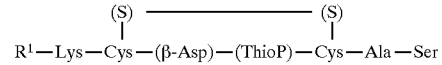

wherein R$^1$ is a substituent of the α-amino group of Lys and is selected from the group consisting of 9-FCA and 1-FCA; and the ε-amino terminal group of Lys is denoted as NHR$^2$, where R$^2$ is H, 1-NaphAc, 2-NaphAc or PhAc.

30. A compound of the formula:

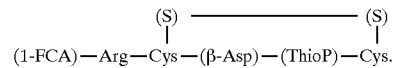

31. A compound of the formula

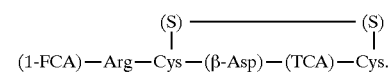

32. A compound of the formula

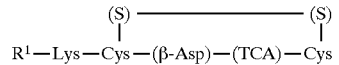

wherein R$^1$ is a substituent of the α-amino group of Lys and is selected from the group consisting of Fmoc, 9-FAc, 9-FCA and 1-FCA; and the ε-amino terminal group of Lys is denoted as NHR$^2$, where R$^2$ is selected from the group consisting of H, 1-NaphAc, 2-NaphAc and PhAc.

33. A compound of the formula:

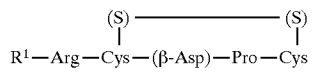

wherein R$^1$ is a substituent of the α-amino group of Arg and is selected from the group consisting of Fmoc, 9-FCA, 1-FCA and 9-FAc.

34. A compound of the formula:

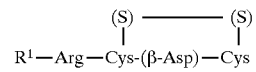

wherein R$^1$ is a substituent of the α-amino group of Arg and is selected from the group consisting of Fmoc, 9-FCA, 1-FCA and 9-FAc.

35. A compound of the formula:

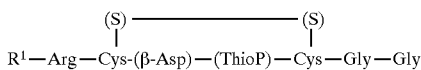

wherein R¹ is a substituent of the α-amino group of Arg and is selected from the group consisting of 1-FCA, 9-FCA, 9-FAc, and Fmoc.

36. A compound of the formula:

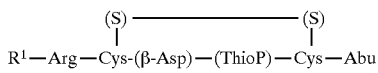

wherein R¹ is a substituent of the α-amino group of Arg and is selected from the group consisting of 1-FCA, 9-FCA, 9-FAc, and Fmoc.

37. A compound of the formula:

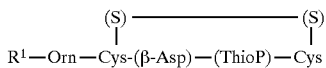

wherein R¹ is a substituent of the α-amino group of Orn and is selected from the group consisting of 1-FCA and Fmoc; and the side chain terminal amino group of Orn is denoted as NHR², where R² is selected from the group consisting of H and PhAc.

38. A compound selected from the group consisting of
(9-FCA)-Arg-Cys*-(β-Asp)-(N-Me-Ala)-Cys*,
(1-FCA)-Arg-Cys*-(β-Asp)-Ser-(ThioP)-Cys*,
(1-FCA)-Arg-Cys*-(β-Asp)-Ser-(ThioP)-Cys*-Ala-Ala,
(1-NaphSO₂)-Arg-Cys*-(β-Asp)-(ThioP)-Cys*-Ala-Ala,
(2-NaphSO₂)-Arg-Cys*-(β-Asp)-(ThioP)-Cys*-Ala-Ala,
(1-FCA)-Arg-Cys*-(β-Asp)-(TCA)-Cys*,
(Fmoc)-Arg-Cys*-(β-Asp)-(Aib)-Cys*,
(Fmoc)-Arg-Cys*-(β-Asp)-(N-Me-Ala)-Cys*,
(Fmoc)-Arg-Cys*-(β-Asp)-(N-Me-Ala)-Cys*-NH₂ and
(Ac)-Cys*-(β-Asp)(αOFm)-(ThioP)-Cys*.

39. A pharmaceutical composition comprising: the compound of claim 1, and a pharmaceutically acceptable carrier.

40. A compound according to claim 1, wherein r=0, m=1, and X¹ is Arg or Lys.

41. A compound according to claim 40, wherein R¹ is selected from the group consisting of Xan, 2-NaphAc, 9-FCA, 1-FCA, 2-NaphCA, Ac, PhAc, 1-NaphSO₂ and 2-NaphSO₂.

42. A compound according to claim 1, wherein
r is 0;
X¹ is selected from the group consisting of a residue of an amino acid and a residue of an amino acid mimetic;
m is 1; and
X² is selected from the group β-Asp, β-Asp(R³), γ-Glu and γ-Glu(R³), wherein R³ is selected from the group consisting of —OR, —NHR and —NRR, wherein R is selected from the group consisting of a hydrogen atom, a lower alkyl, an aryl, an arylalkyl, a cycloalkyl a heteroaryl-lower alkyl and a heterocyclic group.

43. A compound according to claim 42, wherein p is 0, q is 1 and X⁴ is selected from the group consisting of Pro, ThioP, Aib, TTC, Asn, TCA, Sar, an N-methylated natural amino acid, Tic and pipecolinic acid.

44. A compound according to claim 43, wherein r=0, m=1, and X¹ is Arg or Lys.

45. A compound according to claim 42, 43 or 44, wherein R¹ is selected from the group consisting of Xan, 2-NaphAc, 9-FCA, 1-FCA, 2-NaphCA, Ac, PhAc, 1-NaphSO₂ and 2-NaphSO₂.

* * * * *

UNITED STATES PATENT AND TRADEMARK OFFICE
CERTIFICATE OF CORRECTION

PATENT NO. : 5,851,329
DATED : December 22, 1998
INVENTOR(S) : LACAGNINA

It is certified that error appears in the above-identified patent and that said Letters Patent is hereby corrected as shown below:

On the title page, item

[73], change "Porta, Checcacci & Botti, Milan, Italy" to --Pirelli Coordinamento Pneumatici S.p.A., Milan, Italy--.

Signed and Sealed this

Twenty-ninth Day of February, 2000

Attest:

Q. TODD DICKINSON

Attesting Officer

Commissioner of Patents and Trademarks